US 7,941,322 B2

(12) United States Patent
Shelton et al.

(10) Patent No.: US 7,941,322 B2
(45) Date of Patent: May 10, 2011

(54) SYSTEM AND METHODS FOR PROVIDING A HEALTHCARE INDUSTRY TRADE SHOW VIA INTERNET

(76) Inventors: John S. Shelton, Memphis, TN (US); H. Stephen Brown, Memphis, TN (US)

( * ) Notice: Subject to any disclaimer, the term of this patent is extended or adjusted under 35 U.S.C. 154(b) by 1359 days.

(21) Appl. No.: 11/040,029

(22) Filed: Jan. 24, 2005

(65) Prior Publication Data

US 2005/0165624 A1 Jul. 28, 2005

Related U.S. Application Data

(63) Continuation-in-part of application No. 09/594,739, filed on Jun. 16, 2000, now Pat. No. 6,847,940.

(51) Int. Cl.
G06F 15/00 (2006.01)
G06F 15/16 (2006.01)
(52) U.S. Cl. .......................................................... 705/2
(58) Field of Classification Search ................... 705/20, 705/2, 3, 26, 27
See application file for complete search history.

(56) References Cited

U.S. PATENT DOCUMENTS

| 4,980,829 | A | | 12/1990 | Okajima et al. |
| 5,490,061 | A | * | 2/1996 | Tolin et al. ................. 704/2 |
| 5,784,546 | A | * | 7/1998 | Benman, Jr. ................ 715/207 |
| 5,809,247 | A | | 9/1998 | Richardson |
| 5,995,119 | A | | 11/1999 | Cosatto et al. |
| 6,009,410 | A | | 12/1999 | LeMole et al. |
| 6,020,884 | A | | 2/2000 | MacNaughteon |
| 6,029,195 | A | | 2/2000 | Herz |
| 6,339,754 | B1 | | 1/2002 | Flanagan et al. |
| 6,489,980 | B1 | | 12/2002 | Scott et al. |
| 6,847,940 | B1 | * | 1/2005 | Shelton et al. ............... 705/26 |
| 2001/0014865 | A1 | * | 8/2001 | Franke .......................... 705/1 |

(Continued)

FOREIGN PATENT DOCUMENTS

JP 408161214 A 6/1996

(Continued)

OTHER PUBLICATIONS

"Alpha Bytes Announces H-NET(R); Full-Service E-Commerce Internet Portal for Vision Care Industry", PR Newswire, p. 2288 (Aug. 1999).

(Continued)

*Primary Examiner* — Gerald J. O'Connor
*Assistant Examiner* — Hiep V. Nguyen
(74) *Attorney, Agent, or Firm* — Stites & Harbison, PLLC; Juan Carlos A. Marquez, Esq

(57) ABSTRACT

A system or method for providing a 3-D virtual healthcare industry trade show via internet including at least one server computer for collecting, assembling, storing, correlating, or otherwise processing information desired by a participant of the healthcare industry, and at least one other computer used by the participant of the healthcare industry connected via internet or intranet to conduct transactions with other participants or exhibitors of the healthcare industry trade show. Other embodiments include means for leaving any facility or any activity in progress and then return to at the same location, timing to continue without starting from the beginning of the visit or activity, means for creating a 3-D virtual Continuing Education facility, and means for disseminating FDA permitted off-label product promotions which are scientific and educational in nature to medical community as delivered by independent third parties in the formats of clinical trials, special studies, and grand rounds.

23 Claims, 23 Drawing Sheets

U.S. PATENT DOCUMENTS

2003/0037109 A1  2/2003  Newman et al.

FOREIGN PATENT DOCUMENTS

WO  WO-00/39694  *  7/2000

OTHER PUBLICATIONS

Jonathan R. Merril et al., "Virtual heart surgery trade show and medical education," Virtual Reality World, Jul.-Aug. 1994, pp. 55-57.

No Author, "Medtrade online at 222.medtrade.com, The official healthcare industry virtual trade show site to be available on SEMCO Productions" Business Wire, Aug. 5, 1996. Retrieved from Dialog File 16, Acct# 04496026.

No Author, "American-Academy of Physician Assistants Chooses Avicenna; Avicenna Reaches 32,000 Registered Users",PR Newswire, Sep. 16, 1996. Retrieved from Dialog File 14, Acct# 0456921.

No Author, "Netscape and Qwest Unveil Plans for Next-Generation Internet Communications," PR Newswire, Sep. 17, 1998. Retrieved from Dialog File 20, Acct# 02840475.

* cited by examiner

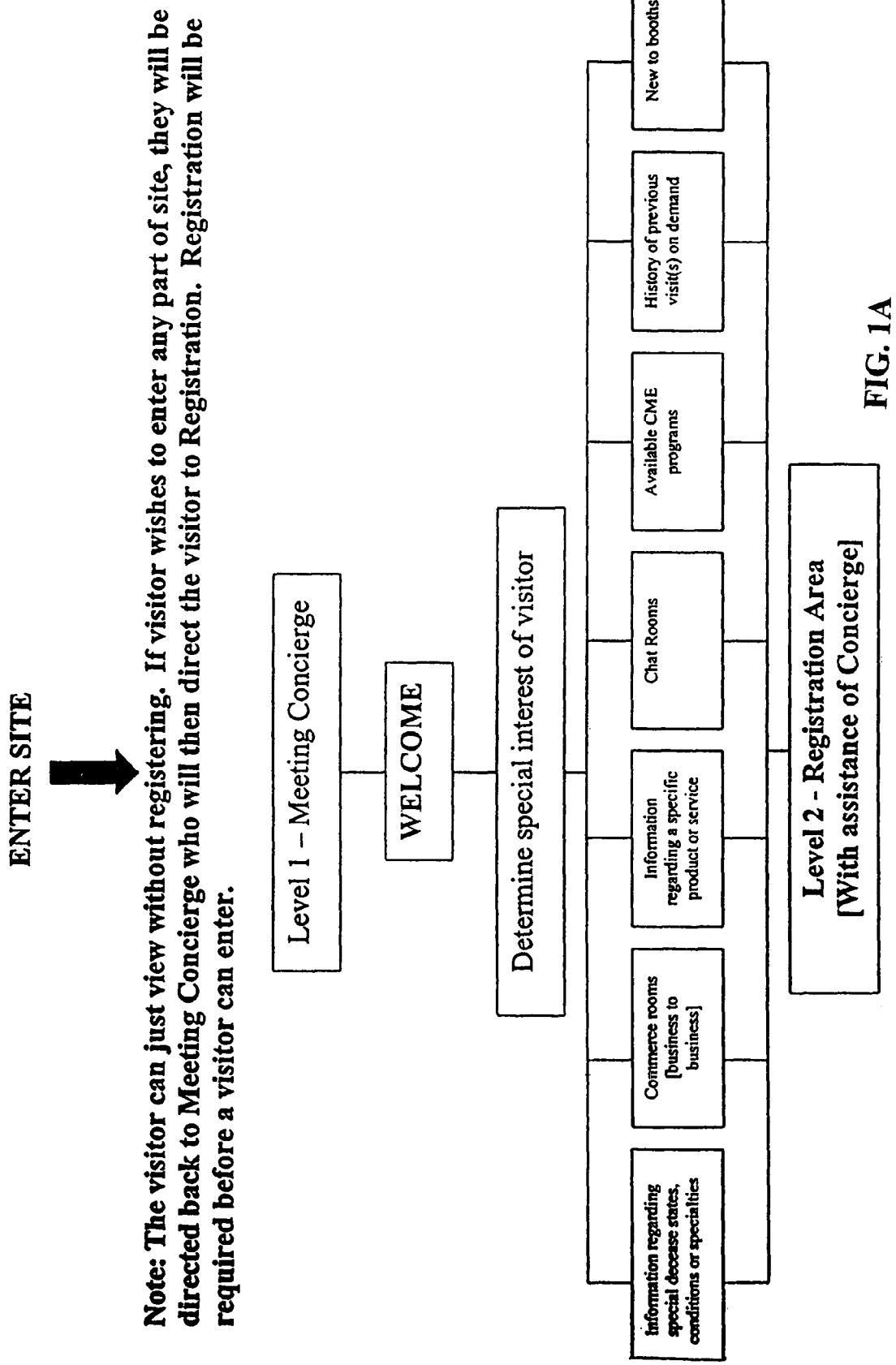

Level 5H – New Discovery Room – A place to present information about new medications, equipment and healthcare services.

SYSTEM AND METHODS FOR PROVIDING A HEALTHCARE INDUSTRY TRADE SHOW VIA INTERNET

This application is a Continuation-in-Part application of U.S. application Ser. No. 09/594,739 filed on Jun. 16, 2000 now U.S. Pat. No. 6,847,940. Priority is claimed based on the parent U.S. application Ser. No. 09/594,739 filed on Jun. 16, 2000.

BACKGROUND OF THE INVENTION

1. Field of the Invention

The invention relates to systems and methods for providing a virtual trade show via internet for healthcare professionals. More particularly, the invention relates to systems and methods providing via internet a virtual trade show for the participants in the healthcare industry, including the participants of any healthcare trade shows, seminars, conferences, etc., especially healthcare professionals.

2. Discussion of the Related Art

A variety of healthcare data management systems have been developed for improving the delivery of healthcare such as U.S. Pat. No. 5,542,420 entitled "Personalized Method and System for Storage, Communication, Analysis, and Processing of Health-Related Data" to Goldman et al. on Aug. 6, 1996 for a personalized prescription as to edibles, U.S. Pat. No. 5,940,802 entitled "Digital Disease Management System" to Hildebrand, et. al. on Aug. 17, 1999 for improving the delivery of healthcare for patients, and U.S. Pat. No. 5,301,105 entitled "All Care Health Management System" to Cummings, Jr. on Apr. 5, 1994 for providing a closed network among insurers and healthcare providers to better manage healthcare utilization and reimbursements. As internet is getting more popular and secured by modern technologies, more such information systems further included an internet-transmitting feature, such as U.S. Pat. No. 5,890,129 to Spurgeon on Mar. 30, 1999, entitled "System for Exchanging Healthcare Insurance Information".

There are many virtual sites related to healthcare, such as "Virtual Medical Center—Martindale's Health Science Guide" at http://www-sci.lib.uci.edu/HSG/Medical.html, but not a virtual healthcare trade show site designed for B2B. As more individual data management systems or virtual sites have been developed for healthcare practitioners, health management organizations, pharmaceutical companies, medical equipment, device and testing manufacturers and suppliers, consumers healthcare products manufacturers, etc. to cover increasing healthcare information in different therapeutic categories, it becomes increasingly difficult for a member of the healthcare industry to find the desired materials in the flood of information. Therefore, most participants still go to visit expensive and time-consuming trade shows, professional conferences, and continuing educational seminars to accomplish their own pre-set agenda as well as explore interactively with other participants to obtain desired information. From the transactional perspective, trade shows facilitate face-to-face contact, promotional sales information, and in some cases actual sales.

In addition, many trade shows emphasize a specific sector or geographic area of the worldwide healthcare industry to educate, promote products and services and promote sales.

In view of the role of trade shows as above-outlined, many companies have attempted to produce a similar environment over the web to take advantage of its low-cost and convenient worldwide entry, and its ease of operation. For example, the Healthcare Convention and Exhibitors Association hosts a site at http://www.hcea.org/ (as visited on Jun. 13, 2000), which Association brings together trade show designers, city and state convention centers and other groups involved in designing, hosting and providing production services to a trade show. The site also solicits participants for a traditional trade show for conventional services to be held in June 2000 in Savannah. Both the exhibitors of the booths and the Attendees to this site will be different from the exhibitors and Attendees of the trade show of the present invention. In hcea.org, the exhibitors are cities desiring to host a trade show, designers, not booths, manufacturers of booths and the Attendees are trade show planners and designers of healthcare manufacturers and suppliers of products and services. As another example, although "American Medical Review Online Tradeshow" http://tradeshows-online.com/american-medical/html/exhibitionhall.htm (as visited on Jun. 13, 2000) offers consumers, not participants of the healthcare industry, each show booth with an introduction video, textual and graphic descriptions of the products or services, an e-mail message box, and a link to the seller's webpage, the booths are simply characterized by products, services, and alternative medicine. The above-mentioned two sites are consumer-oriented, namely business-to-consumer (B2C). In addition, both of the above-mentioned sites have data structures and functions that are overly-simplified and so limited that they can hardly help anyone obtain his/her desired information efficiently. U.S. Pat. No. 5,966,130 titled "Integrated Virtual Networks" to Benman, Jr. on Oct. 12, 1999 describes a system allowing a participant to attend a trade show as it happens with live or virtual imagery. However, it fails to provide many characteristics of a traditional trade show desired by the participants of the healthcare industry.

Currently, there is not a healthcare tradeshow facilitating a business-to-business e-commerce platform for the healthcare participants to allow healthcare manufacturers and suppliers of products and services to provide content, community and commerce to healthcare providers including, but not limited to physicians, doctors, dentists, nurses, veterinarians, pharmacists, managed care organizations, insurers, pharmacy benefit managers, clinics, nursing homes, hospitals, specialty pharmacy networks, pharmacies, drug wholesalers, medical schools, veterinary schools and dental schools.

SUMMARY OF THE INVENTION

It is a purpose of this invention to provide members of the worldwide healthcare industry 24-hour access to healthcare manufacturers and healthcare suppliers of products and services to provide content, community and commerce, . . . via internet real time (live) or virtually without either visitors or exhibitors required to travel or maintain a physical presence for sales, marketing or exchanging technical or market knowledge.

It is another purpose of this invention to provide easily searchable information categories for a healthcare industry visitor to obtain his/her desired information efficiently except for those intentionally blocked or access-limited via verification or authorization procedures.

It is another purpose of this invention to provide a virtual environment where one group of participants may encounter other participants who would not interact with one another but for the existence of this internet healthcare trade show.

It is another purpose of this invention to present relevant information and internet content about products and services, including textual, graphic, and audio description, vital transactional and credit information to facilitate electronic business-to-business (B2B) and business-to-participants of the healthcare industry (B2P) transactions of healthcare products or services. Necessary security measures will be taken to protect proprietary information.

It is another purpose of this invention to verify the authentication of the Attendee. It is another purpose to verify the credit of the Attendee on certain transactions, activities or services.

It is another purpose of this invention to provide feedback about the quality of products/services on information based on the participants' evaluations, etc.

It is another purpose of this invention to actively promote or market products/services to any participant in countries with or without sufficient internet infrastructure. The web host in countries without sufficient internet infrastructure may take risk as well as commission for such activities based on agreements.

It is still another purpose of this invention to provide Attendees with customized on-line distance learning or telemedicine arrangements.

It is still another purpose of this invention to provide state of the art video-conferencing to ensure Attendees get the real sense of live participation.

It is still another purpose of this invention to attract healthcare experts from around the world to play an integral role in the planning of the trade show's scientific presentations. There is no such international forum in existence today and the procedure will provide a unique opportunity for Attendees to the site to benefit from the experience and insight of these experts.

It is still another purpose of this invention to foster global commerce between exhibitors and Attendees by providing a platform in which to showcase medical products and services, medical institutions, clinics and facilities in different parts of the world. Via digital technology Attendees to the site can directly see and learn about unique treatment environments, procedures, and personnel in locations far from their home base.

It is still another purpose of this invention to virtually detail healthcare products and services, including prescription drugs to healthcare professional Attendees over the Internet.

It is still another purpose of this invention to virtually provide over the Internet continuing medical information to healthcare professionals from an Internet site not controlled or influenced by any manufacturers of medical equipment, devices, or pharmaceutical products.

It is still another purpose of this invention to have a virtual concierge or helper that will assist the Attendees determine the Attendees' special interest, help the Attendees register, help the Attendees find specific information, locations, or areas of interest within the trade show and to provide the Attendees with a history of any previous visit.

It is still another purpose of this invention to provide Attendees information regarding special disease states, conditions or specialties.

It is still another purpose of this invention to provide Attendees an update on what is new at the trade show, since the Attendees' last visit.

It is still another purpose of this invention to provide Attendees with the information regarding specific products or services.

It is still another purpose of this invention while welcoming the participant to the trade show to provide one or more promotional messages or other information.

It is still another purpose of this invention to allow Attendees access to experts.

It is still another purpose of this invention to have such trade show features that include satisfaction surveys, request for suggestions on improvements, information on current continuing education programs, information on future continuing education programs that may be of interest to the Attendee, tracking receipts of goods and services and continuing education credits, request e-mails on various topics, including, but not limited to, documents or information that may be related to areas that such Attendees visited.

BRIEF DESCRIPTION OF THE DRAWINGS

The foregoing and other objects, features and advantages of the invention will become apparent from the following more particular description of preferred embodiments of the invention, as illustrated in the accompanying drawings, in which.

DESCRIPTION OF THE PREFERRED EMBODIMENTS

Figure 1B:
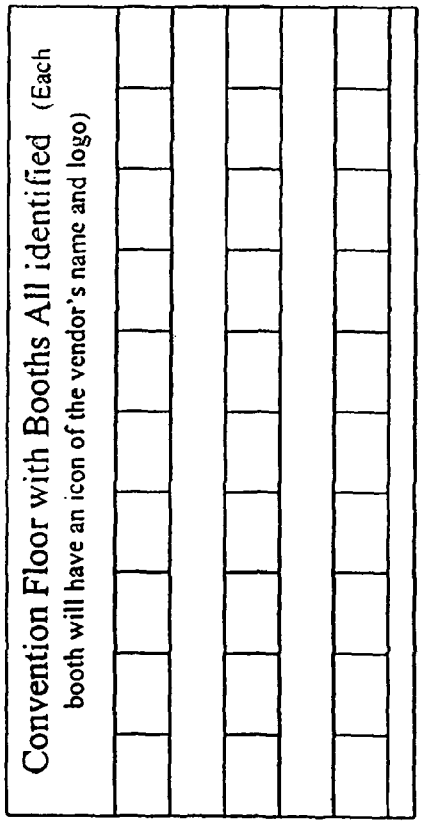
FIG. 1 is a diagram illustrating one embodiment of the process flow of selected access levels of the present invention when deployed in a virtual trade show environment.

In order to more clearly and concisely describe the subject matter of the claims, the following definitions are intended to provide guidance as to the meanings of specific terms used in the following written description. Also it is to be understood that the phraseology or terminology employed herein is for the purpose of description and not of limitation. As used herein:

"Healthcare": The prevention, treatment, and management of illness and the preservation of mental and physical well-being through the services offered by the medical and allied health professions (as defined in *The American Heritage® Dictionary of the English Language, Third Edition* copyright©1992 by Houghton Mifflin Company).

"Healthcare industry" includes the industries of or relating to healthcare.

"Participants of the healthcare industry" include but not limited to individual healthcare providers further including but not limited to physicians, osteopaths, dentists, veterinarians (Vets), optometrists, podiatrists, providers of homeopathic medicine, physician assistants, nurses, residents, pharmacists and psychologists; institutional healthcare providers further including but not limited to medical and nursing schools, hospitals, clinics, diagnostic and treatment centers, health maintenance organizations (HMO) and preferred provider organizations (PPO); pharmaceutical companies; medical equipment, device and testing manufacturers and suppliers; job recruiters; consumers of healthcare products and services; managed care organizations; pharmacy benefit managers healthcare consultants; pharmacoeconomics and formulary managers, etc.

"Attendee" includes participants of the healthcare industry who visit the trade show.

"Exhibitors" are the sponsors of the virtual booths and are generally pharmaceutical manufacturers or medical equipment or device manufacturers or suppliers, consumer healthcare products manufacturers or suppliers, health management organizations, health insurance companies, healthcare providers, and managed care organizations.

Health Maintenance Organization (HMO): A managed care organization that arranges a wide spectrum of healthcare services which commonly include hospital care, physicians' services and many other kinds of healthcare services with an emphasis on preventive care (See Glossary of Healthcare Terms, http://www.cigna.com/healthcare/glossary.html visited on Jun. 4, 2000).

Preferred Provider Organization (PPO): A network of healthcare providers which provide managed care to patients with generally higher benefit coverages and lower deductibles (See Id.).

"Communication Vehicles" include a variety of channels for communication during the visit to the Medtradeshow as well as after the Attendees leaves the site. These vehicles for transmitting textual, 2-D, or 3-D imagery signals will include but are not limited to e-mail, ICQ, IRC, animation or virtual reality which may then be carried via pagers, internet telephony (e.g., Voice over IP or VoIP), telephone, satellite, public utility lines, fiber optics and cable. Communication Vehicles will support the functions of concierge, eLERTS (instant audio or video announcements), detailing, celebrity Pop-Ups, Case conferencing, Tele-Medicine, Continuing Education, Advisory Panel/Needs Assessment, Office Management, and/or Disease Management.

ICQ: ("I Seek You") A conferencing program for the Internet which provides interactive chat, e-mail and file transfer and can alert you when someone on your predefined list has also come online (See Tech Encyclopedia, http://www.techweb.com/encyclopedia/ visited on Jun. 4, 2000).

IRC, Internet Relay Chat: Computer conferencing on the Internet. There are hundreds of IRC channels on numerous subjects that are hosted on IRC servers around the world. After joining a channel, your textual or graphical messages are broadcast to everyone listening to that channel (See Id.).

"Medtradeshow" is a description of the invention; provided, however, any descriptive phrases or domain names may be used for the invention, a virtual healthcare trade show, including but not limited to Medtradeshow.

"DEA" is the abbreviation of the "Drug Enforcement Administration" under the U.S. Department of Justice which is responsible for enforcing the controlled substances laws and regulations of the United States and assigns a provider number to all authorized medical prescribers of controlled drugs (See http://www.usdoj.gov/dea/).

"Enterprise Data Access" and "EDA" Popular middleware software from information builders that runs on more than 35 platforms and provides a common interface between client requests to more than 80 different database and file types. It allows queries on different types of databases at the same time (See Id.).

"Artificial Intelligence" implies human-like intelligence. Devices and applications that exhibit human intelligence and behavior including robots, expert systems, voice recognition, natural and foreign language processing. It also implies the ability to learn or adapt through experience.

Medtradeshow will serve as a new platform for "business-to-business" and "business-to-Attendees" tradeshows occurring in the healthcare field via the Internet. The basis for Medtradeshow has been the worldwide explosion in the amount of health-related information, products, and services that are now available to the marketplace. One effect of this increase is the inability of healthcare providers to receive and process this data in a timely fashion.

One traditional way to gain exposure to information, products, and services is to attend a tradeshow where one can learn about products and services and also attend educational lectures and courses. Unfortunately attending tradeshows is difficult for most healthcare providers for travel and lodging is expensive and professional and personal demands leave little time to attend these sessions. In addition all of these tradeshows are held thousands of miles away from the majority of those who would attend if they had a more immediate access. It is also ironic that while technology is changing quickly in the healthcare arena most healthcare products/service suppliers are still forced to employ large international sales forces to do a majority of the day-to-day selling.

Medtradeshow provides more efficient ways of both providing information and making the sales function more efficient. Medtradeshow creates a virtual reality via the Internet, where information exchange and/or transactions between healthcare providers and healthcare manufactures, suppliers and experts can occur 24 hours a day, every day of the year. In addition since Medtradeshow is virtual, any healthcare provider with access to a computer and modem can participate, thus eliminating the traditional constraints of time and financial limitations.

Not only does Medtradeshow create a unique environment for "business-to-business" and "business-to-Attendees" transactions, it also provides unique options designed to help those attending the healthcare tradeshow to navigate around the virtual convention floor. These features include a booth with multiple rooms; a tradeshow Concierge; instant audio and/or video announcements via eLERTS; direct selling via detailing; a unique Pop-Up system of interaction with experts and Attendees on the convention floor; opportunities for Attendees to gain insights into treatment via presentation of case reports; the use of special advisory panels to help assess the needs of those visiting the site and create education programs to meet those needs; and instant education credits.

This virtual Medtradeshow provides each Attendee with (1) options to receive information about the content, products and/or services showcased in each booth presented in print, voice, and/or video format; (2) an opportunity to receive the history of each visit. Thus the Attendee will know which booths were visited and what transpired in each booth, thus assisting him/her during their current visit. This virtual Medtradeshow provides each Attendee with the opportunity to receive (1) an email summarizing and highlighting portions of the conference proceedings; (2) an opportunity to learn about products and services; (3) an opportunity to receive the following but not limited to product monographs, to order samples of medications, to obtain reprints of articles from the scientific literature, newsletters, scientific monographs, supplements, audiotapes, videotapes, via the communication vehicles. Specifically, the communication vehicles support textual, 2-D, or 3-D imagery or animation to be displayed at the request of an Attendee. In addition, such communication vehicles support inputted signals via touch screens, keyboards, handwriting recognition, voice recognition means, and other inputting means or their combinations. As part of the conference and meeting room infrastructure, the communication vehicles supported by the latest in technology features are available in all areas of Medtradeshow to be triggered by click an icon which brings up a drop down menu for selecting at least one of different vehicles and at least one of the participants to communicate with. More than one communication vehicles may be deployed at the same time. For example, Medtradeshow plays per-recorded corresponding information when a selected one of displayed 3-D facilities is being shown.

In one embodiment of the invention, Shockwave, Flash, and Web Services are applied to provide a 3-D representation of the conference and meeting rooms of Medtradeshow (a.k.a. MedFair) and its surroundings, including expansive views of the skyline and waterfront. Shockwave is a technology developed by Macromedia, Inc. that enables Web pages to include multimedia objects. Shockwave supports audio, animation, video and even processes user actions such as mouse clicks. Flash is also developed by Macromedia, Inc. which is a bandwidth friendly and browser independent vector-graphic animation technology. As long as different browsers are equipped with the necessary plug-ins, Flash animations will look the same. With Flash, Medtradeshow can draw animations or import other vector-based images. Web Services are a family of protocols and standards used for exchanging data between applications. Software applications written in various programming languages and running on various platforms can use web services to exchange data over computer networks like the Internet. This interoperability (e.g., between Java and Python, or Windows and GNU Linux applications) is due to the use of open standards.

Medtradeshow utilizes Director-Shockwave as its main interface. Embedded within Shockwave are Flash movies. Some of these Flash movies apply Flash's built-in functionalities for connecting to a web service provided by Medtradeshow's internal databases. Menus, etc are filled with information based upon the web service. Upon clicking on an object, parameters are sent out of Flash, then back into Director-Shockwave. A program was written using Director's built-in parseXML function for the communication via XML between the internal database and web services. Additionally, Medtradeshow's database fills fields in the host html file when the Attendee first logs in. These values are stored and used by Director to identify the Attendee and send the Attendee to a particular room/hall of Medtradeshow.

Figure 11:
FIG. 11 is the front webpage of Medtradeshow.
Figure 12:
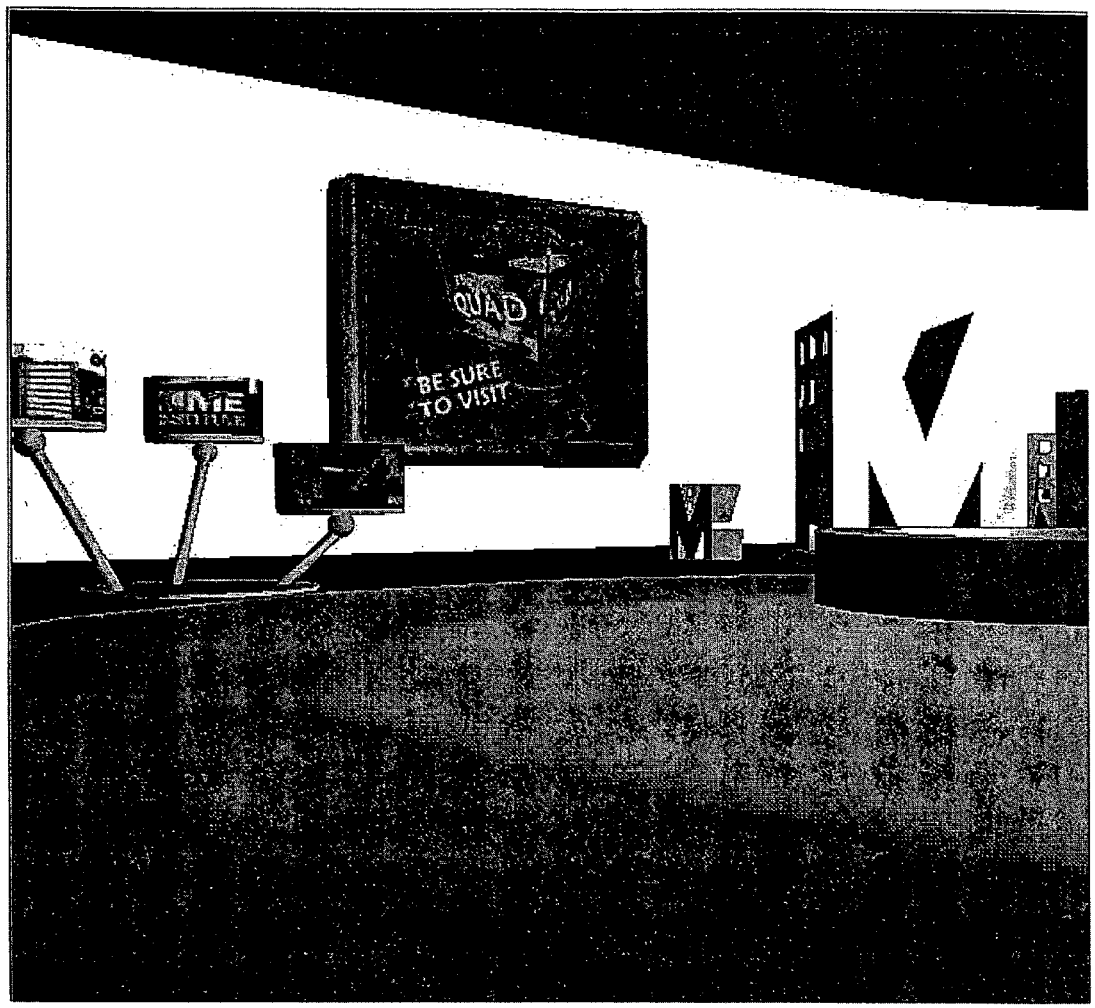
FIG. 12 shows the lobby of Medtradeshow.
Figure 13:
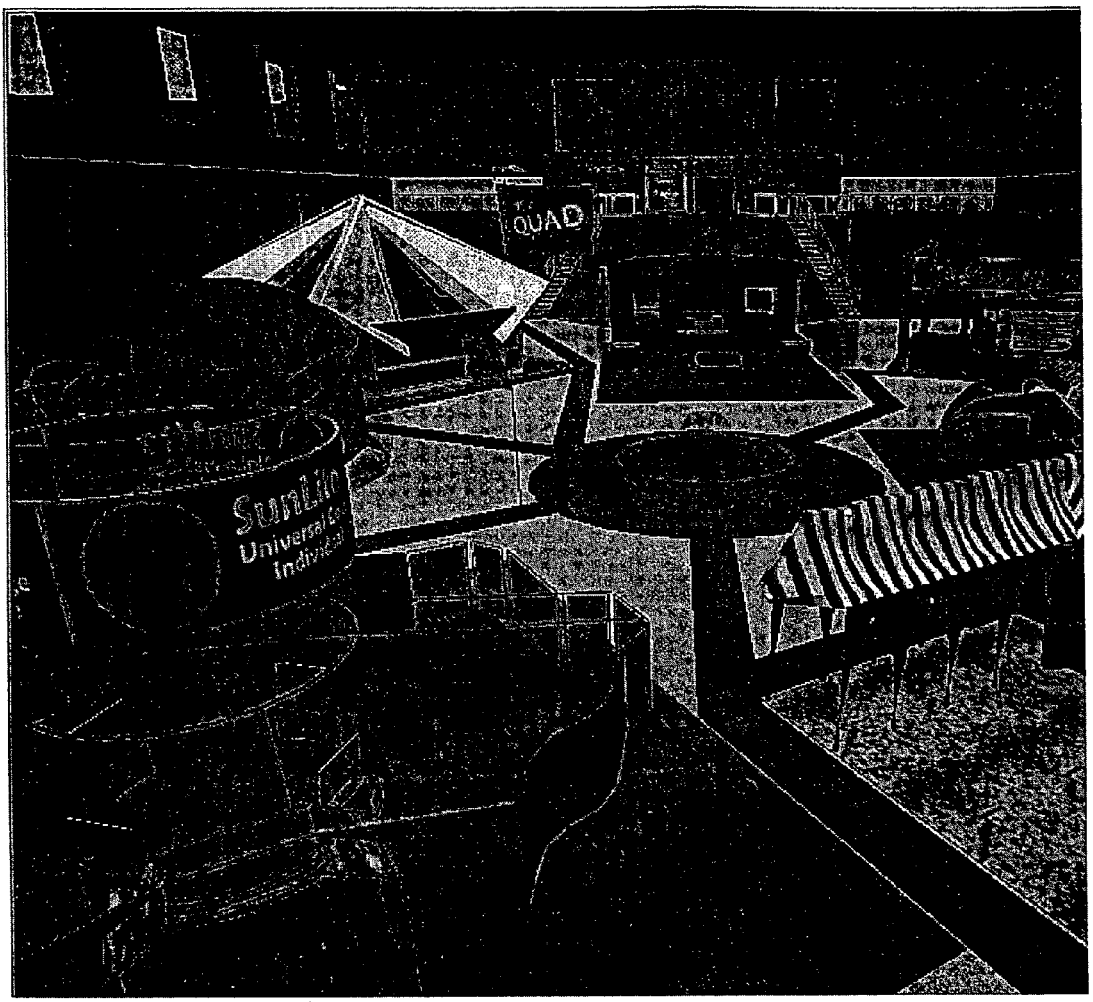
FIG. 13 shows the exhibition hall of Medtradeshow.
Figure 14:
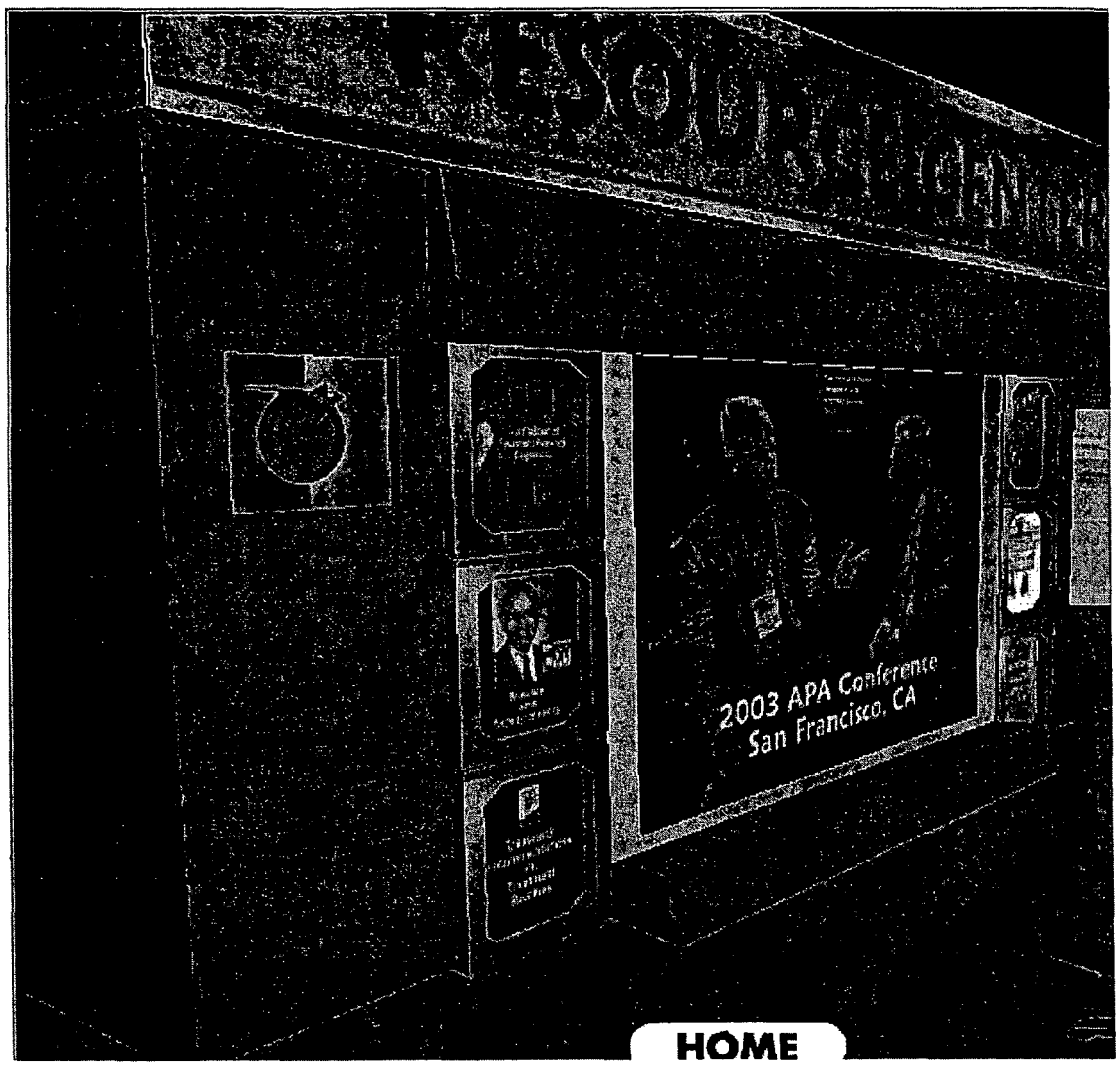
FIG. 14 shows a resource center in the exhibition hall of Medtradeshow of FIG. 13.

In FIG. 11, the top banner shows a side view of Medtradeshow, and at the left-had side, a prospective view of a 3-D virtual trade center/facility is provided, which houses exhibitions and offices for participants of the healthcare industry stands right behind a pier for boats or helicopters landing, or other ground and air transportation and accommodations. Medtradeshow is a virtual med tradeshow designed to offer a one-stop resource for the participants of the healthcare industry to manage updated informational and intricate transactional details on-line. FIG. 12 shows the lobby of Medtradeshow with a display screen showing the "QUAD" booth as "BE SURE TO VISIT" as well as three 3-D kiosks for different rooms/halls of Medtradeshow. An Attendee can click the display screen to go to the booth or the kiosks to go to the rooms/halls, such as the exhibition hall shown in FIG. 13. Except booths, there is a resource center within the exhibition hall as shown in FIG. 14. The resource center has a center screen displaying materials of past events such as 2003 APA Conference in San Francisco, Calif., or promoting coming events. There are also six smaller screens on the sides of the center screen displaying highlights of different rooms/halls.

As shown in FIGS. 1-10, the present invention incorporates optional functional features, including Concierge, detailing, celebrity Pop-Ups, Case conferencing, Tele-Medicine, Continuing Education, Advisory Panel/Needs Assessment, and Office Management and Disease Management into various Medtradeshow booths, Rooms or Halls to facilitate the above-mentioned functions at different times.

Medtradeshow offers the exhibitors opportunities to update the information available in the booths by revising from a remote computer. Additionally, the Exhibitors can link certain keywords, paragraphs, or articles in the display boards to a on-line information source, such as a website or a database, to synchronize the contents. For example, the word of a new drug embedded in a display board may be linked to the website of the manufacturer so as to trigger a new notice regarding drug as soon as it occurs.

Figure 2:
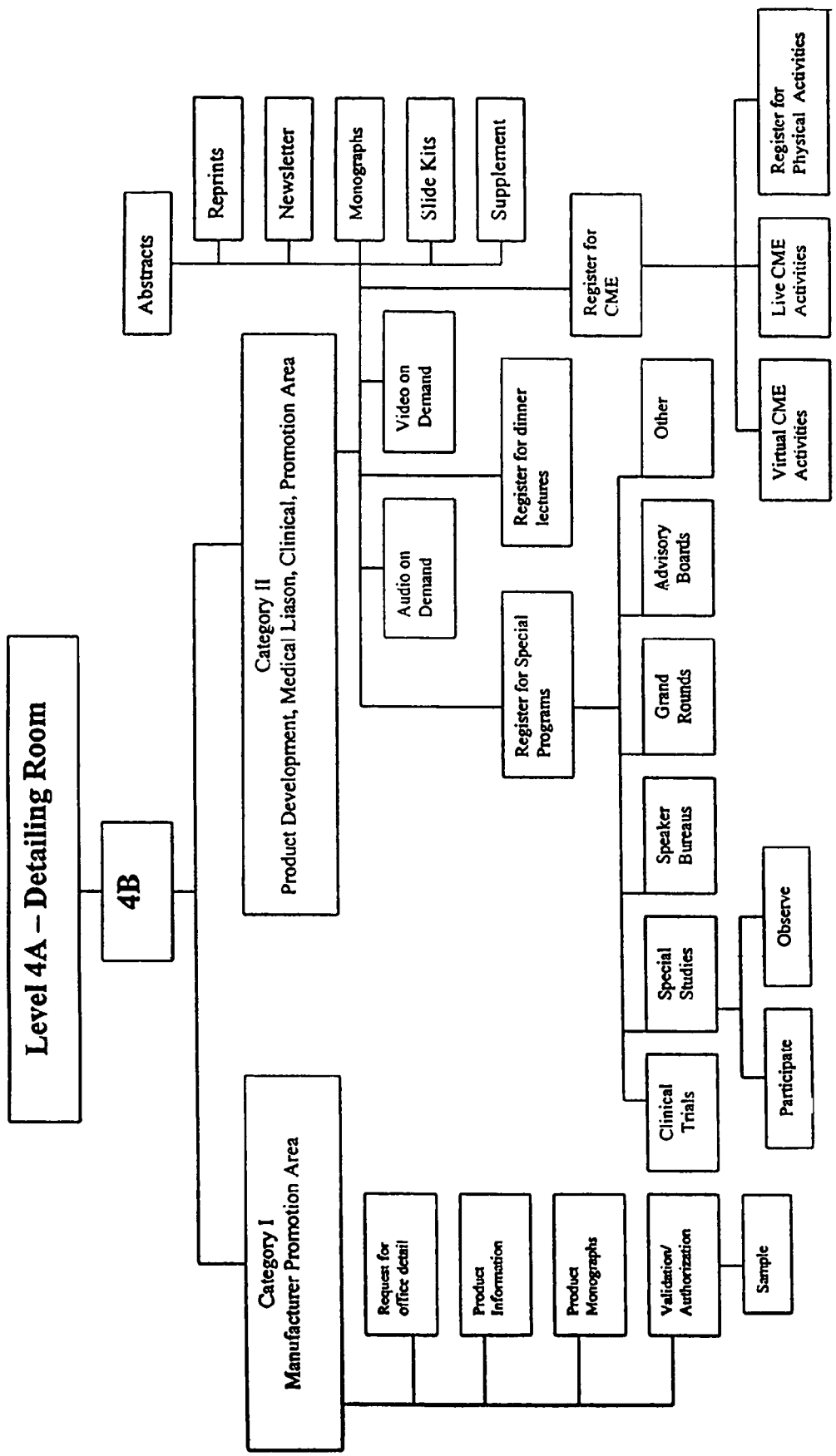
FIG. 2 is a diagram illustrating process flow depicting one embodiment of the detailing feature of the present invention when deployed in a virtual trade show environment.
Figure 3:
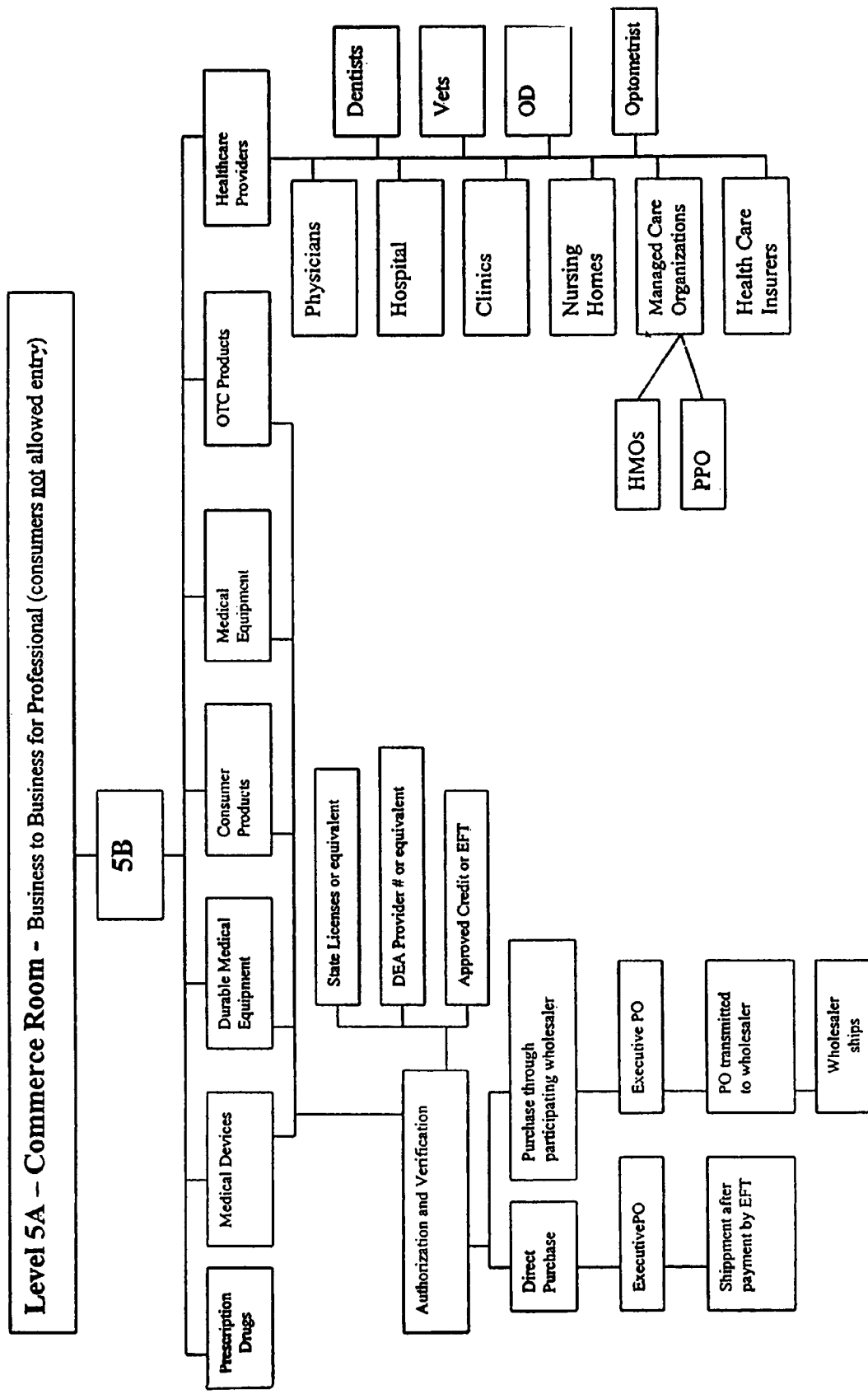
FIG. 3 is a diagram illustrating process flow depicting one embodiment of the Commerce Room feature of the present invention when deployed in a virtual trade show environment.
Figure 4:
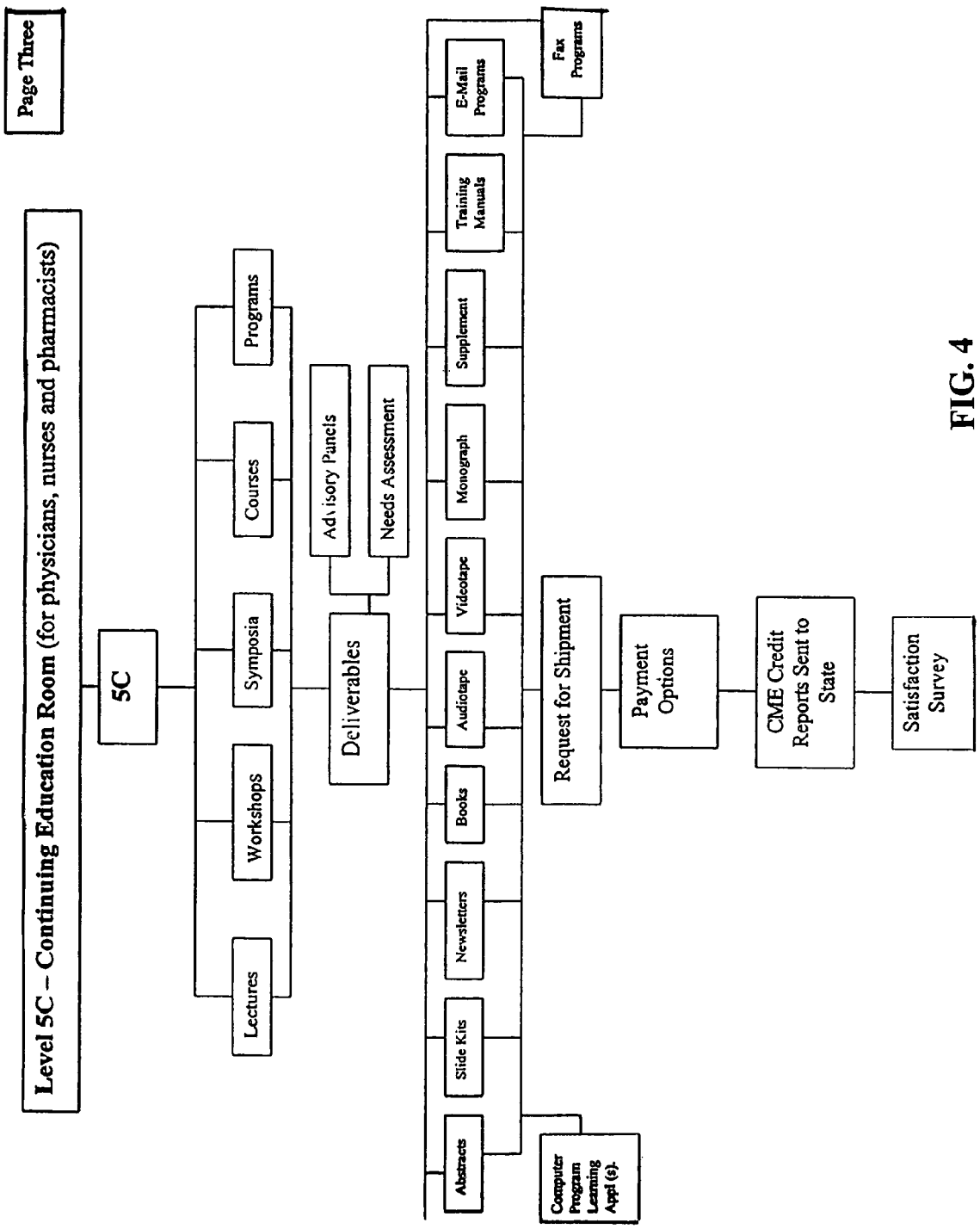
FIG. 4 is a diagram illustrating process flow depicting one embodiment of the Continuing Education Room feature of the present invention when deployed in a virtual trade show environment.
Figure 5:
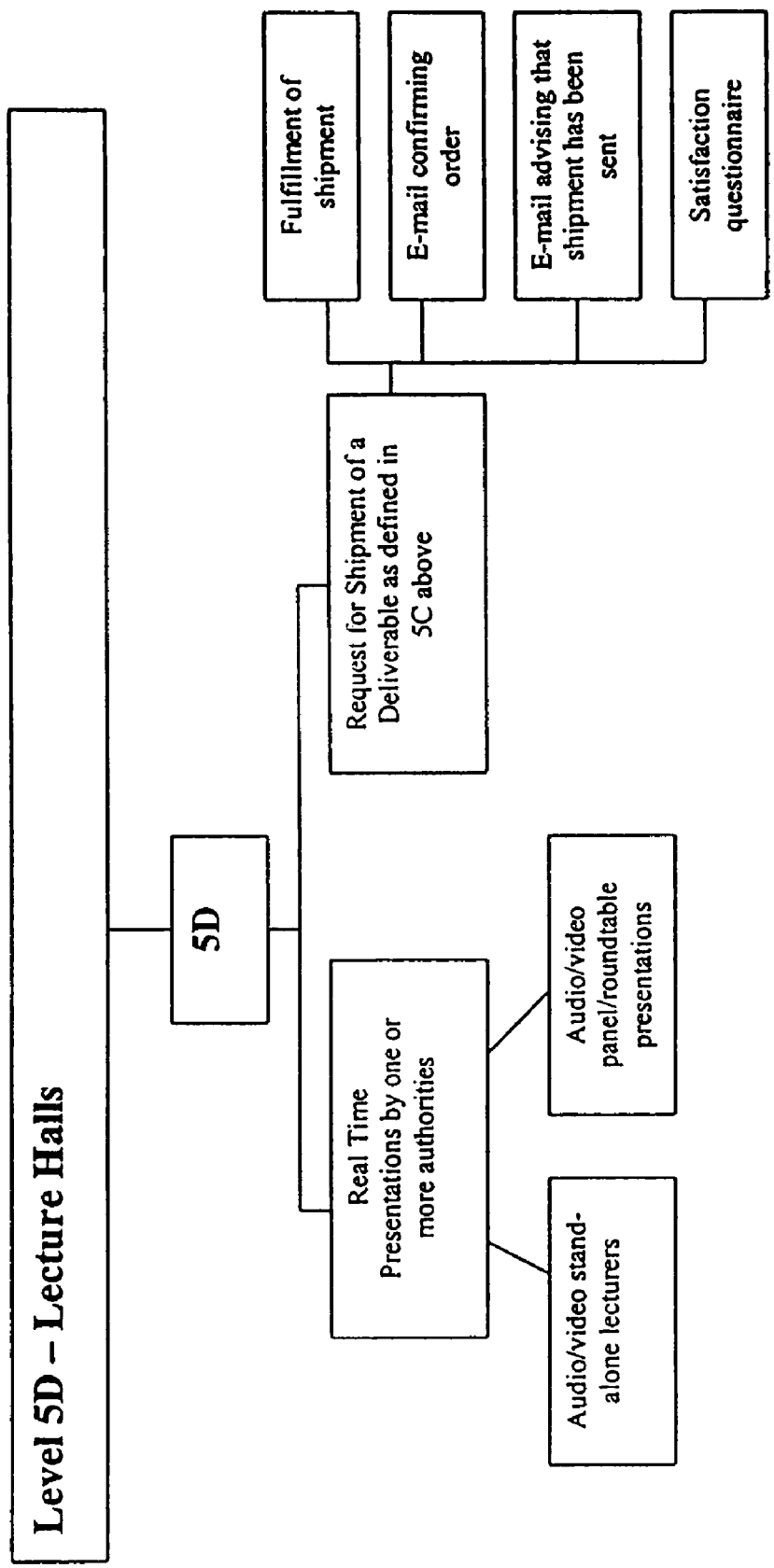
FIG. 5 is a diagram illustrating process flow depicting one embodiment of the Lecture Halls feature of the present invention when deployed in a virtual trade show environment.
Figure 6:
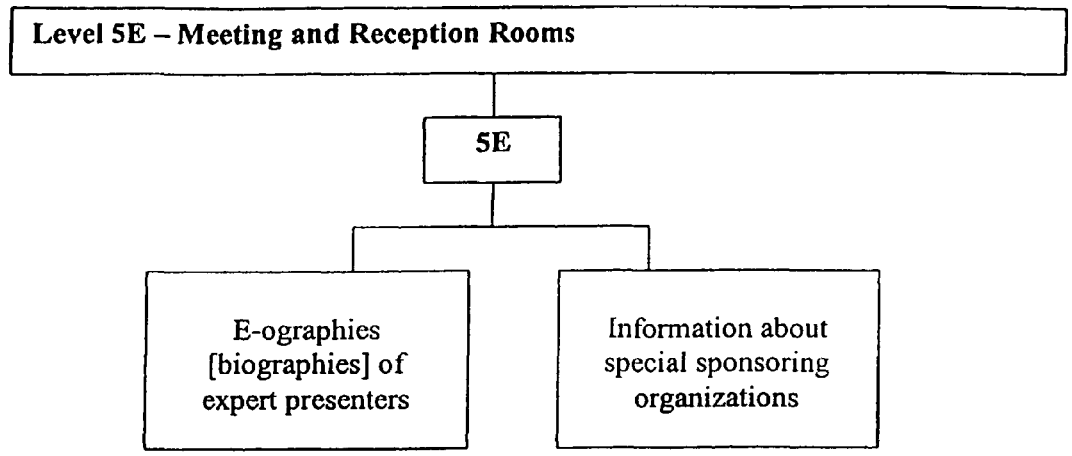
FIG. 6 is a diagram illustrating process flow depicting one embodiment of the Meeting and Reception Room feature of the present invention when deployed in a virtual trade show environment.
Figure 7:
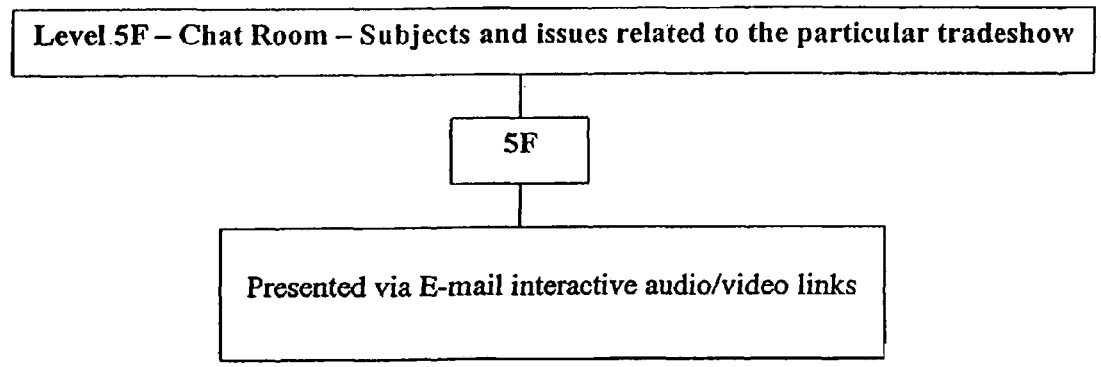
FIG. 7 is a diagram illustrating process flow depicting one embodiment of the Chat Room feature of the present invention when deployed in a virtual trade show environment.
Figures 8, 9:
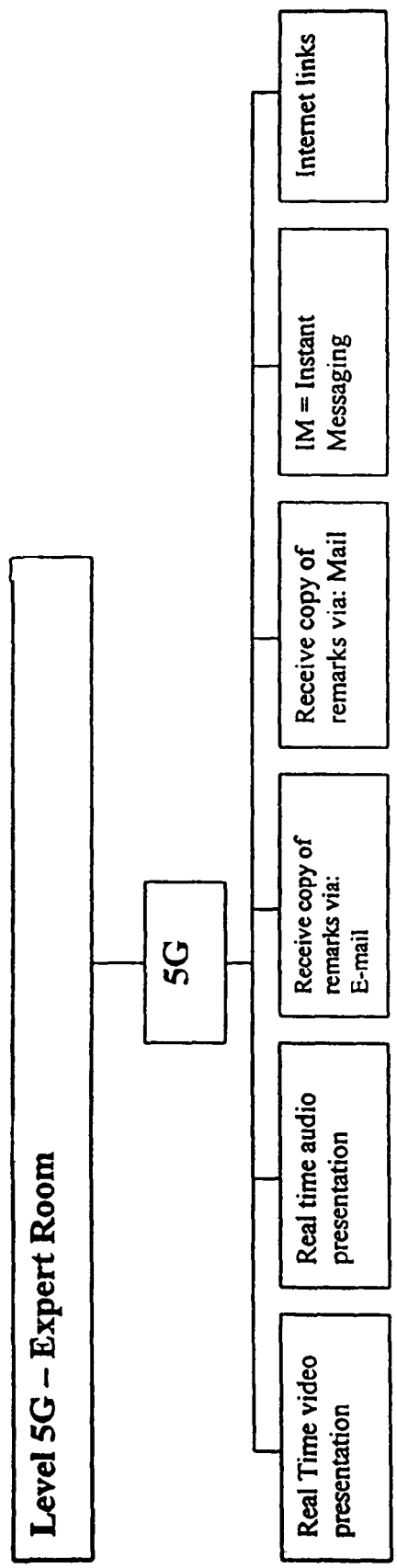
FIG. 8 is a diagram illustrating process flow depicting one embodiment of the Expert Room feature of the present invention when deployed in a virtual trade show environment.
FIG. 9 is a diagram illustrating process flow depicting one embodiment of the New Discovery Room feature of the present invention when deployed in a virtual trade show environment.
Figure 10:
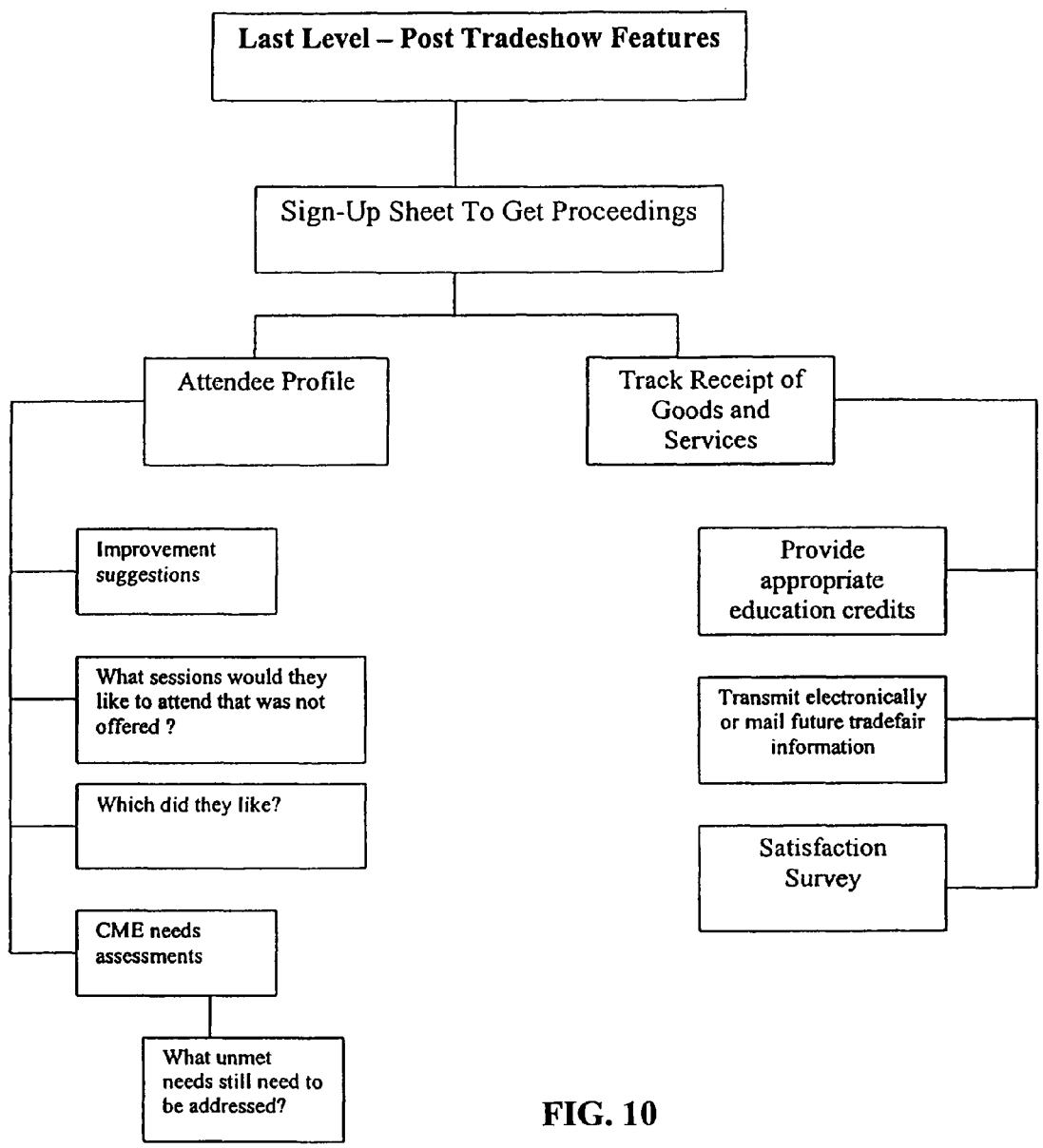
FIG. 10 is a diagram illustrating process flow depicting one embodiment of the Post Medtradeshow feature of the present invention when deployed in a virtual trade show environment.

To ensure each Attendee is appropriately authorized under applicable laws and regulations to access certain rooms or information, verification and authorization procedures are provided whenever and wherever necessary. For example, manufacturers will wish to block certain healthcare professionals who are not appropriately licensed for receiving samples as shown in FIG. 2.

The Attendee can click a menu icon at the corner to bring out a menu bar or call up a Concierge menu screen to browse, search, bookmark any facility, or to ask for recommendation, or to view the facilities visited by the Attendee previously. In addition, the Attendee may choose to leave or sign off any facility of any activity in progress and then return or sign in to such facility or activity to resume the visit or activity at the same place, timing to continue to the visit or activity without starting from the beginning of such visit or activity.

Concierge

Figure 1C:
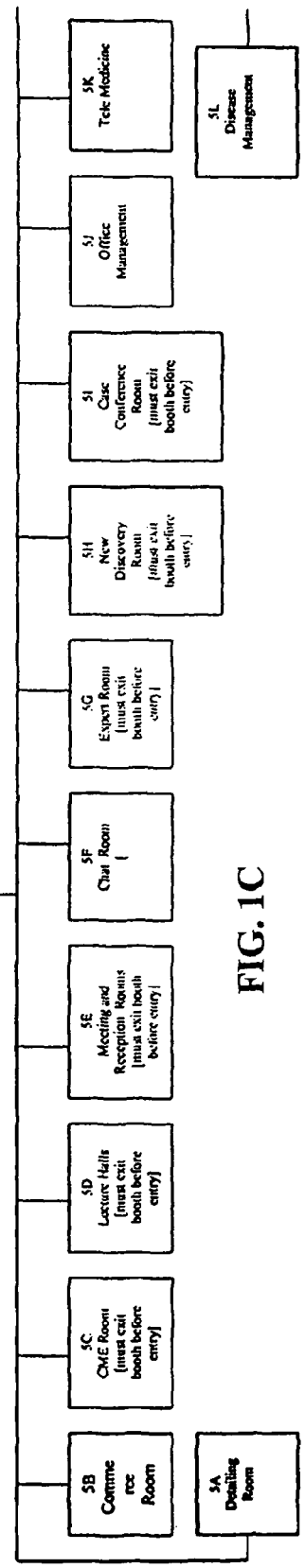

The "concierge" features, as shown in FIG. 11 and the process flow in FIG. 1, will include, but not be limited to providing general programmed information about the Medtradeshow and, through a series of prompts provide Attendees with directions to the areas within the various booths where qualified experts will answer specific questions about medications, medical devices, service suppliers and institutions. The virtual concierge will first welcome the Attendee and then provide one or more promotional messages or other information. The virtual concierge will also assist each Attendee, determine the Attendee's special interest, help the Attendee register, help the Attendee find specific information, locations, or areas of interest within the trade show and to provide the Attendee with a history of any previous visit as well as to update on what is new at the trade show, since the Attendee's last visit.

In one embodiment, this concierge is generated by a sophisticated and subtle information storage and retrieval system equipped with artificial intelligence. In other words, the concierge will ask you what help you need and automatically call in the appropriate applications to aid you in solving your problem. For example, a Medtradeshow Attendee may ask the concierge which areas within the various booths would have information about the availability of a particular US medication in a foreign country. Another typical question could be about therapies provided at a particular institution or about a new device for measuring blood sugar. In another embodiment, the concierge may, with appropriate consent of the Attendee, track Attendee's activities while visiting. Such information, with appropriate consent, may be processed then forwarded (complying with Federal and State Privacy and Confidentiality Laws) to certain Medtradeshow exhibitors.

Beside the communication, as stated above, the concierge also collects data by tracking the Attendees' activity since their registration. As the Attendee moves around the Medtradeshow floor their activity is captured. A formal report summarizing the Attendee's movements, including locations, duration of each stay is prepared and under the appropriate circumstances may be transmitted to appropriate Medtradeshow exhibitors (complying with Federal and State Privacy and Confidentiality Laws).

In terms of visual appearance, the concierge may be shown as a figure of any sex, race, height, weight, eye or hair color.

Pick of the Month

Medtradeshow offers a drop-down screen when an Attendee click on the icon of "Pick Of The Month". The Attendee can choose the Picks most frequented browsed by individual healthcare providers, institutional healthcare providers, pharmaceutical companies; medical equipment, device and testing manufacturers and suppliers; job recruiters; managed care organizations; pharmacy benefit managers healthcare consultants; pharmacoeconomics and formulary managers, etc. The Picks may be articles, classes, lectures, booths, rooms, or halls in Medtradeshow. Then the Attendee can choose further by a sub-category e.g., psychiatrists within the category of individual healthcare providers. Via the drop-down screen, the Attendee can also choose the Picks recommended by Exhibitors which sponsor the virtual booths and pay additional fee for a higher ranking in the Pick list. The Attendee may select Picks by categories of exhibitors, such as pharmaceutical companies; medical equipment, device and testing manufacturers and suppliers; etc. Then the Attendee can choose further by a sub-category of pharmaceutical companies, such as companies supplying a generic drug (a chemical name).

eLERTS

The eLERTS will, in part, be instant messages that drive traffic to specific booths. The eLERTS are designed to grab the attention of the Attendee and their function will include, but not be limited to, providing information about products and services including references to scientific articles about a particular subject, symposia, disease state management information within a specific booth and reasons for an Attendee to stop by such booths. The eLERTS are designed to bring a sense of realism to the site and can be programmed to provide a true virtual experience. The eLERTS can be transmitted by a written instant message or through an instant video presentation. Thus the Attendee may learn of a new product introduction, that a new booth has just been constructed and might be useful to visit, or that a symposium has been cancelled and a new lecture is available.

The eLERT is also designed to be a maintenance program providing continuous communication to those who have attended the Medtradeshow providing information about new booths, lectures, workshops, and symposia. In addition the recipient will have the opportunity to order samples, purchase goods and services and order copies of enduring materials. In addition there will an opportunity to offer suggestions as to future topics to be covered in the scientific programs.

Detailing

DETAILING in the physical world is carried out by a sales representatives who visit with healthcare providers promoting products and services. These sales representatives use support information obtained from formal or informal, official or non-official information sources, including but not limited to medical journals, company data, information from drug trials, expert advisors, information from meetings, product samples, promotional materials, detail tools and detail aids. The inventor proposes to virtually provide the same services to the healthcare provider over the Internet. The inventor has applied for trademark protection for "detailing" to describe virtual healthcare DETAILING. The detailing according to the invention is different from "e-tailing" defined as 'selling of retail goods on the Internet' at http://www.whatis.com/detailing.htm (visited Jun. 4, 2000). In particular, detailing is synonymous with business-to-business (B2B) or business-to-participants of the healthcare industry (B2P) transactions rather than business-to-consumer (B2C) transactions.

As shown in FIG. 2, healthcare products or services were divided into two categories for marketing purposes: Category I [Manufacturer Promotional Area] includes those that have been approved by the U.S. Food & Drug Administration (FDA) specific disease or condition. And category II [Product Development, Medical Liaison, Clinical, Promotional Area] includes permitted off-label promotions that are scientific and educational in nature that will be disseminated to the medical community via independent third parties in the formats of clinical trials, special studies, grand rounds, etc. For example, a pharmaceutical manufacturer would not be permitted to compare its products against another manufacturer; however, a scientific journal article appearing in a peer reviewed Medical Journal could be provided to an Attendee. Such scientific article would be available from the Detail Room in Category II, Category I as an example may have Product Information that is approved by the FDA.

For example, if a psychiatrist would like to learn information about the use of a certain psychotropic medication for the treatment of an illness for which it is not marketed, they would be directed to the "Category II" promotion area which is separated from the "Category I" area. In this promotion area, they would receive scientific information derived from reports in medical journals, meetings, poster presentations, and other sources.

Not only a pharmaceutical manufacturer may initiate distributing a scientific journal article appearing in a peer reviewed Medical Journal to an Attendee, but also the Attendee may request or search such detailing information made available by the pharmaceutical manufacturer in Medtradeshow.

Grand Rounds Room

Interactive grand rounds will be moderated by distinguished experts for physicians, medical students and other selected health professionals. At these sessions actual cases will be discussed and the experts will explain their suggested diagnosis and treatment alternatives.

Speaker Bureaus Room

In this room healthcare providers have the opportunity to offer their services to talk with their colleagues about the diagnosis and treatment of a particular disease.

Celebrity "Pop-Up" Mechanism/Expert Room

"Celebrity Pop-Up" allows spontaneous interaction between subject experts and Medtradeshow Attendees. This interaction will occur when the experts randomly pop-up on the Medtradeshow floor to talk with the Attendees. When these chance meetings occur the Attendee can choose from a series of programmed questions to ask the expert. The virtual Medtradeshow provides each Attendee with an opportunity to meet scientific experts via e-mail, ICQ, real time audio or video presentations in selected language(s). The subject matter for these questions will be based on timely topics and will be created with the assistance of the expert advisory board.

The experts are also available in the Expert Room where Attendees may ask questions.

E-Commerce Room

The E-Commerce Room limits purchases to specific authorized buyers. Each buyer is verified and authenticated by various methods including but not limited to a screening process that compares the buyer's state medical license number and the buyer's DEA number with an up-to-date database that contains both. In addition, after each buyer is verified and authenticated, each buyer must have an approved method of payment such as ("EFT") Electronic Funds Transfer, Business Credit Card, Debit Card or other method of payment.

The virtual Medtradeshow will track the receipt of information ordered while on-site, send an e-mail confirming order placed by the purchaser, send an e-mail to the purchaser when the items have been shipped, and provide each Attendee with an opportunity to obtain information in another room.

Continuing Education Hall

The Continuing Education hall provides each Attendee with an opportunity to register for special programs, dinner lectures or virtual continuing education activities for Attendees. The Attendees will obtain continuing education credits for attending lectures, workshops, and symposia. The Continuing Education hall also provides opportunities of obtaining continuing education via newsletters, books, audiotapes, videotapes, monographs and supplements. In particular, the information provided in the Continuing Education hall is not controlled or influenced by any manufacturers of medical equipment, devices, or pharmaceutical products. Such a characteristic distinguishes the Continuing Education hall from the Category II Detailing Room and the E-Commerce Room.

The Continuing Education hall is developed with input from Special Advisory Panels and from input from the Attendees as to what information they wish to learn about (also known as Needs Assessment). In the physical world, continuing education programs focus on the appropriateness of clinical decision making and implementation of these decisions which are condition specific, procedure specific, or address important functions of patient care, such as medication use, infection control, patient assessment, etc. The Continuing Education Programs are designed to evaluate the processes or outcomes of care associated with the delivery of clinical services and/or pharmaceutical products and/or medical equipment in order to continuously improve patient health outcomes. This invention is unique in the use of advisory panels and Attendees' needs assessments to help design the events occurring in the continuing education hall.

Figure 15:
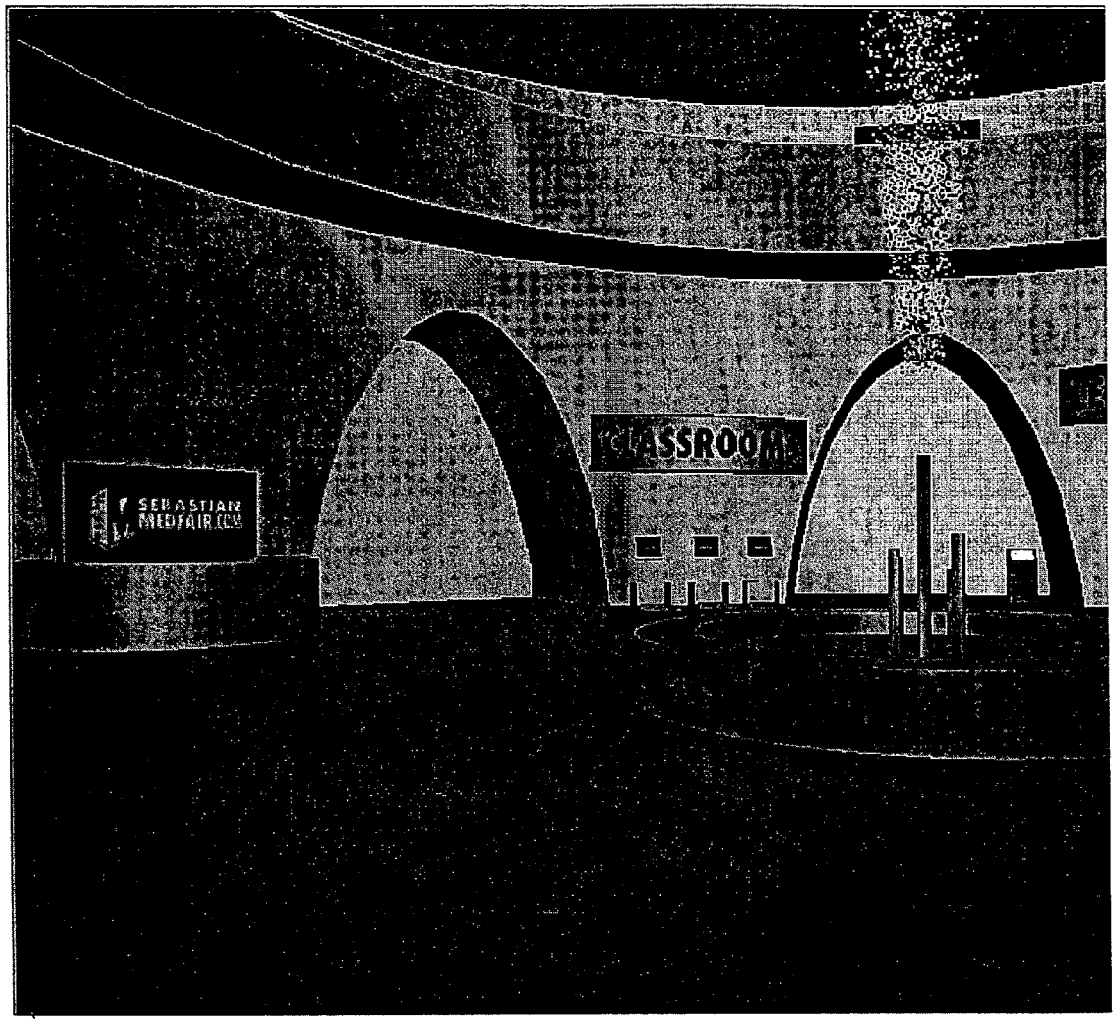
FIG. 15 shows the Continuing Education hall of Medtradeshow.
Figure 16:
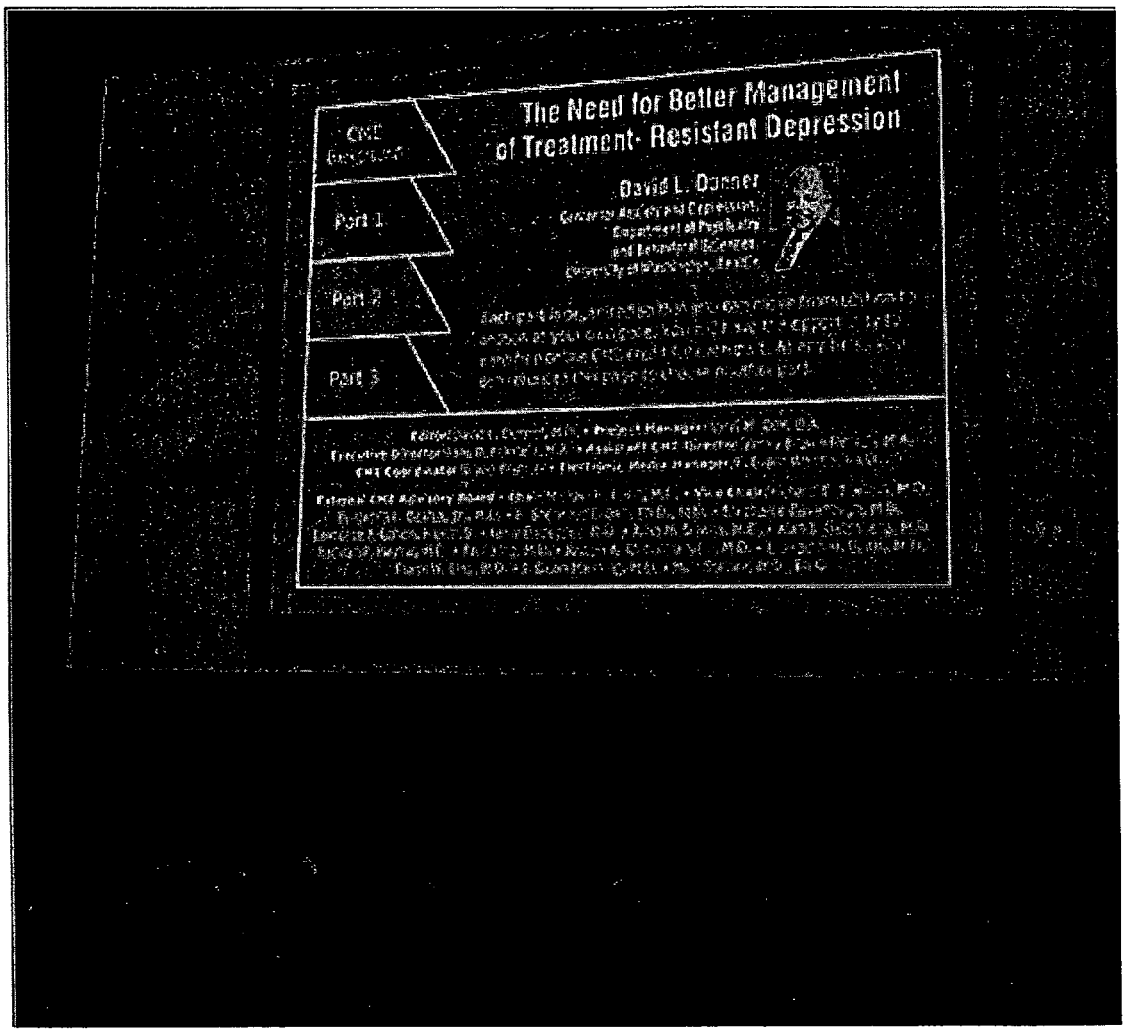
FIG. 16 shows a LECUTUREHALL area the Continuing Education hall of Medtradeshow.
Figure 17:
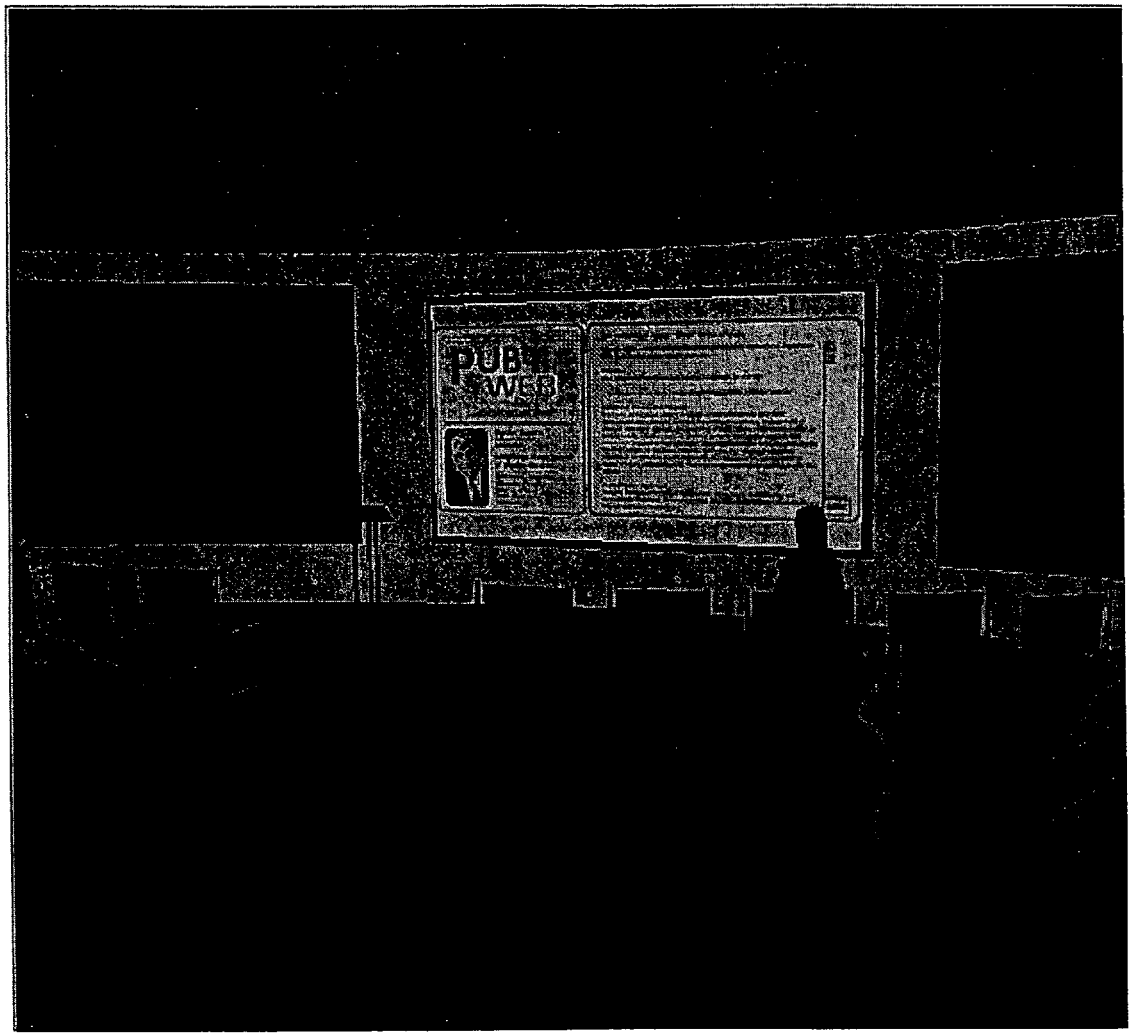
FIG. 17 shows a CLASSROOMS area the Continuing Education hall of Medtradeshow.
Figure 18:
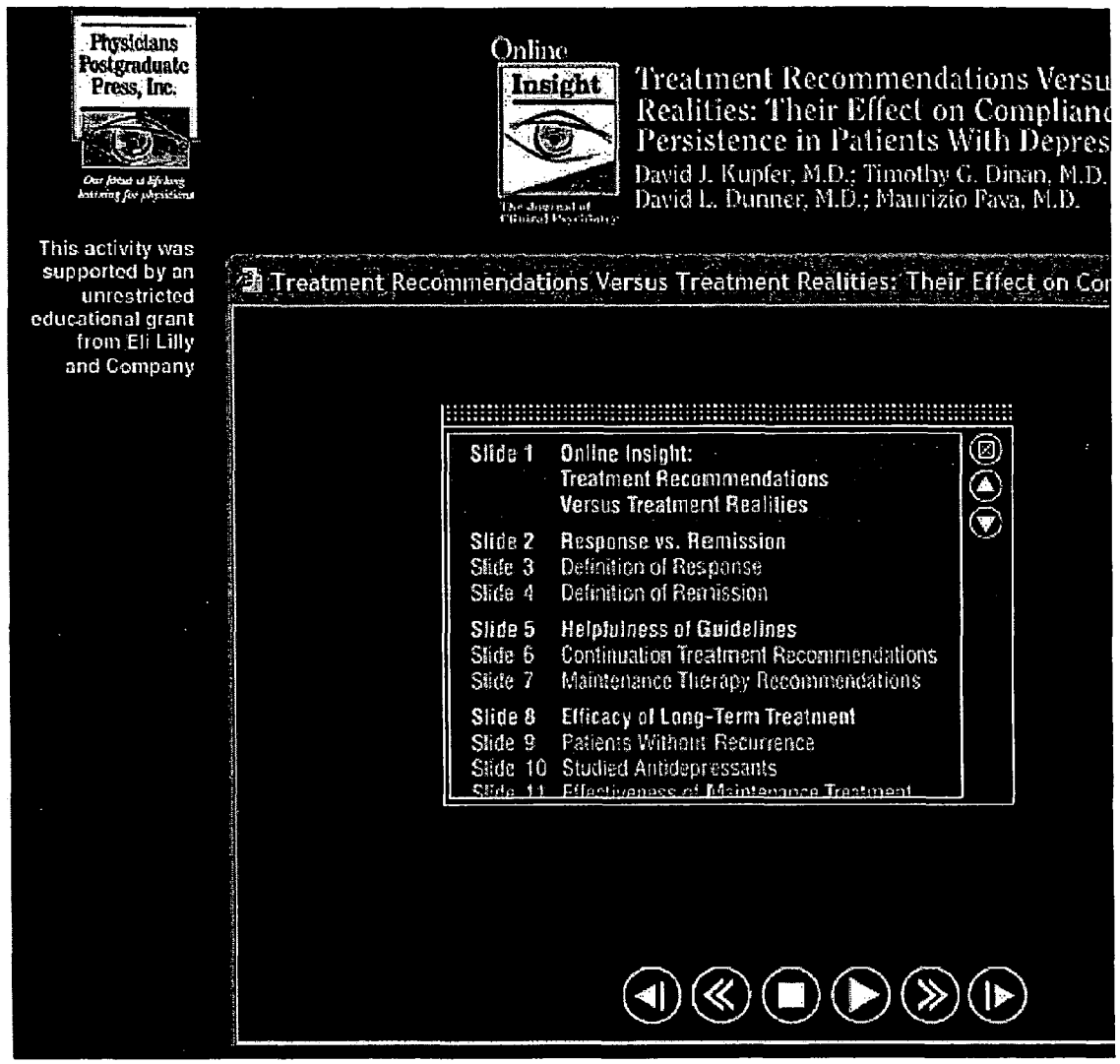
FIG. 18 shows a sub-screen of class outline of an on-going class held in a CLASSROOMS area of FIG. 17.

In one embodiment of the invention (FIG. 15), the Continuing Education hall includes at least a LECUTUREHALL area and a CLASSROOMS area. By clicking one of the computers shown in front of LECUTUREHALL area, another window will be brought up to show the 3-D presentation as shown in FIG. 16 with the recorded speech. By clicking one kiosk in front of the CLASSROOMS area, another window will be brought up to show the 3-D classroom as shown in FIG. 17 with a sub-screen on the top showing the presentation outline (FIG. 18) of the on-going class held in the classroom The outline can be clicked to be scroll up or down for different slides or screenshots in conjunction with the recorded speech corresponding with each slide or screenshot.

Figure 19:
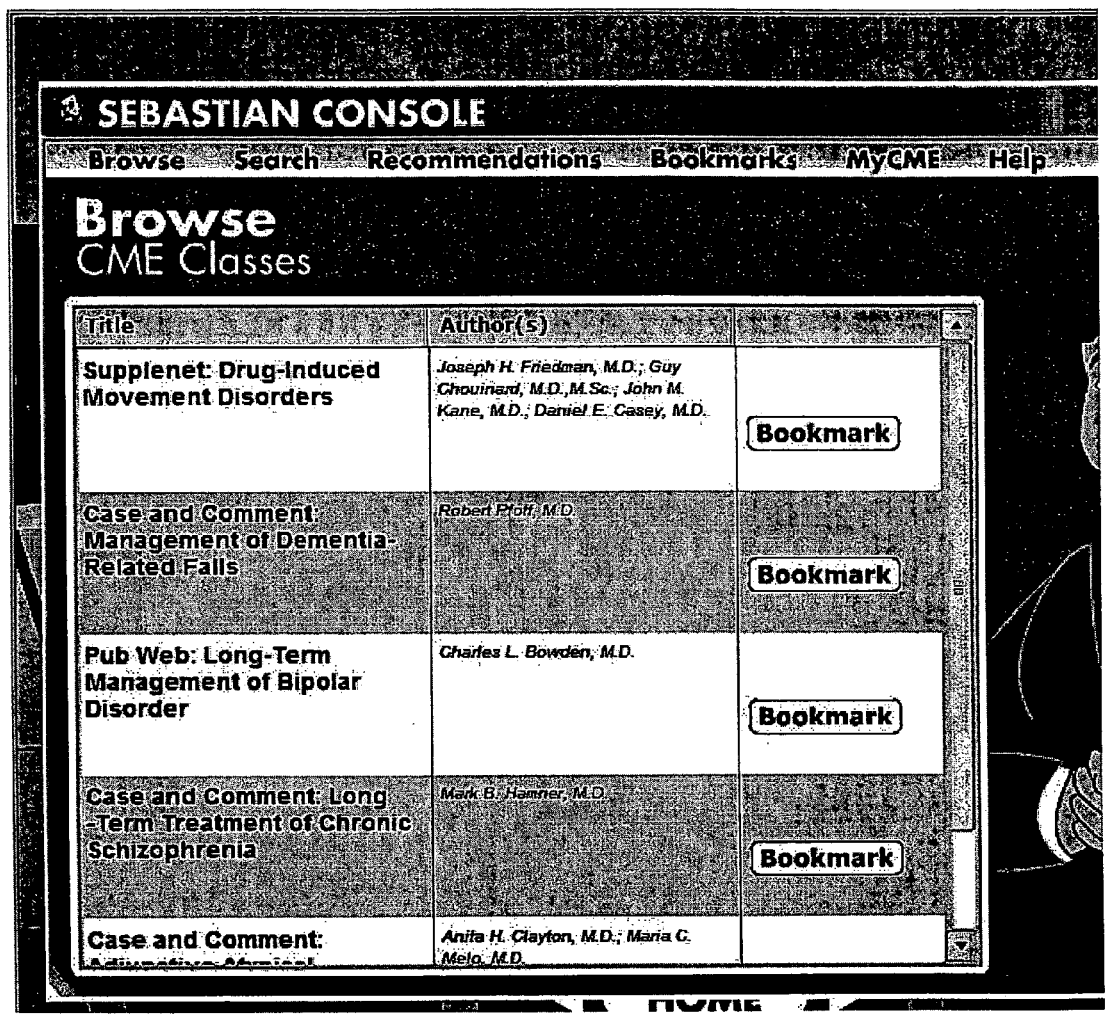
FIG. 19 shows a Concierge menu screen available in a CLASSROOMS area.

The Attendee can click a menu icon at the corner to bring out a menu bar or call up a Concierge menu screen as shown in FIG. 19 to browse, search, bookmark available classes or lectures, or to ask for recommendation, or to view the classes or lectures taken by the Attendee previously.

The Continuing Education hall will also allow an authorized Attendee to sign up to attend a live continuing education program in person at the location that such program is being conducted. Via a drop down menu, an Attendee may just bookmark a webpage or click On Demand to come back later from the beginning of a Continuing Education activity. Alternatively, the Attendee may choose to leave the Continuing Education activity in progress and then return to such Continuing Education activity to resume the activity at the same place, timing to continue to the end of such activity without starting from the beginning of such activity.

The Continuing Education hall also includes Post Medtradeshow Features, such as satisfaction surveys, request for suggestions on improvements, information on future continuing education programs, information on other present continuing education programs that may be of interest to the Attendee, tracking receipts of goods and services and the rewarding of continuing education credits, request e-mails on various topics, including, but not limited to, documents or information that may be related to areas that such Attendee visited.

Medtradeshow determines behavioral outcomes as a result of the Continuing Educational activities by comparing surveyed results before and after attending the activities. For example, an Attendee was surveyed before and after a continuing educational event about diagnosis of a child suspected of suffering from ADHD. The Attendee replied by interviewing the child and family members with non-structural questions before the continuing educational event, but replied that the Attendee adopted Kiddie-SADS presented in the activity one month after attending the continuing educational activity. Kiddie-SADS is a structured psychiatric instrument designed to obtain severity ratings of symptomatology, and assess current and lifetime history of psychiatric disorders.

PPP Booth

Figure 20:
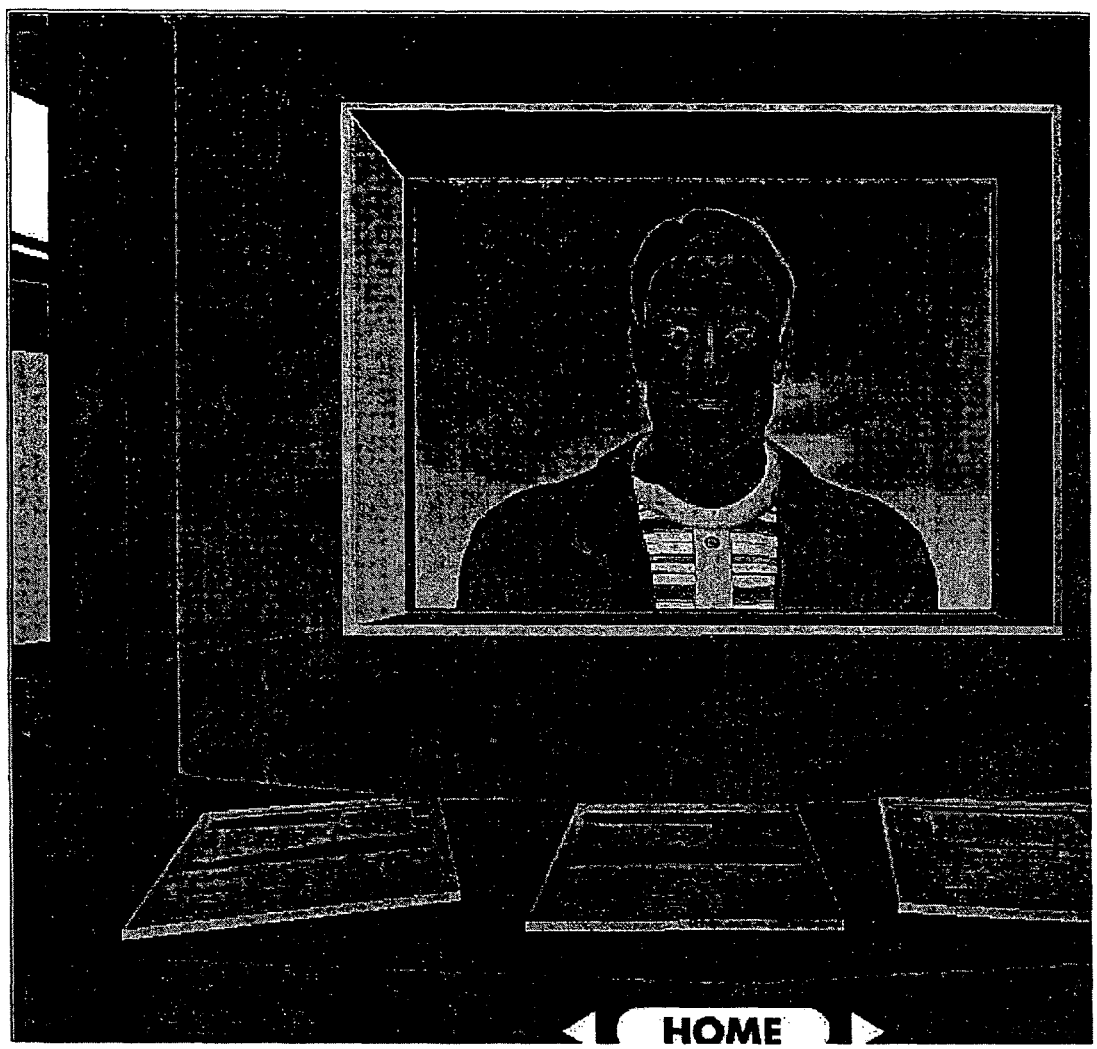
FIG. 20 shows a sample 3-D exhibition booth in Medtradeshow.
Figure 21:
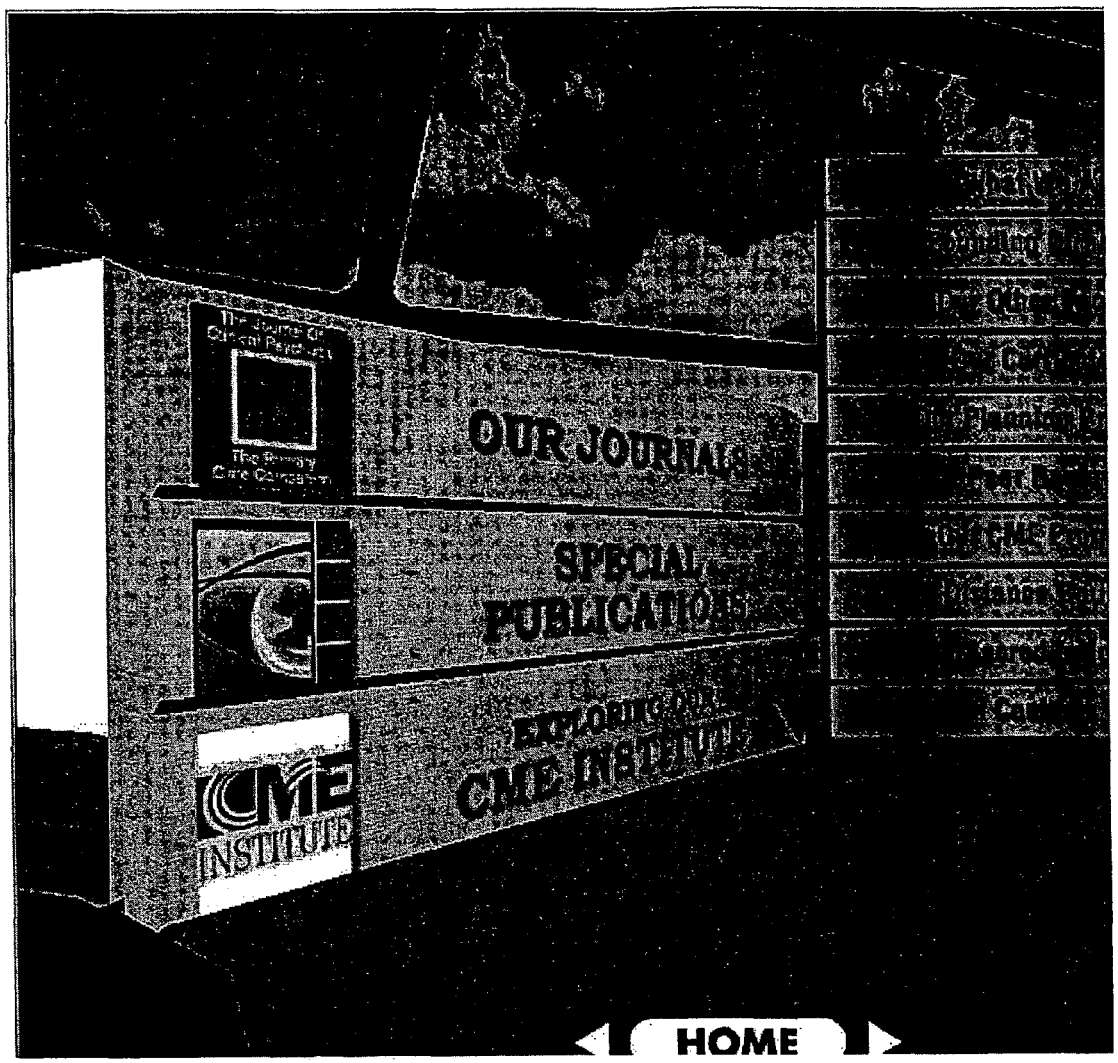
FIG. 21 shows a multi-media board in the 3-D exhibition booth of FIG. 20.

It is a sample 3-D exhibition booth of a medical education provider PPP, which has its own host shown in the main screen in FIG. 20. The host starts narrating the services provided by PPP as along as an Attendee click to visit the booth. Within the booth, there is a multi-media board displaying with three subjects (OUR JOURNALS, SPECIAL PUBLICATIONS, EXPLORING OUR CME INSTITUTE) each with a respective menu screen at the right side as shown in FIG. 21. For example, if the last subject is chosen, the menu screen at the right side displays "What We Are," "Founding Directors," "Our Other Faculty," "Our Curriculum," "Our Planning Process," "Peer Review," "Our CME Program," "Distance Rounds," "Accreditation," And "Contacts."

Case Conference Room

The Case Conference Room is a part of the convention floor and is designed to include, but not limited to, the presentation of case reports. These cases will be prepared by experts who will use them to demonstrate key elements in the diagnosis and treatment of a particular disease, syndrome, drug reaction, allergy, injury or other medically related problem. Those visiting this room will learn about the particulars of the cases. Situational variables surrounding each case may be different. Cases that may appear similar at first, when examined more closely reveal themselves to be different due to differences in time, location, conditions, and individuals involved.

In addition, the presentations can be structured to allow the expert to propose a diagnosis and treatment regimen that can then be compared to that proposed by the Attendee. The access can be either synchronous or asynchronous. Synchronous accesses allow interaction between expert(s) and Attendee(s) to take place simultaneously. On the other hand, asynchronous accesses allow experts and or/Attendees to respond at their own convenience.

Poster Room

Figure 22:
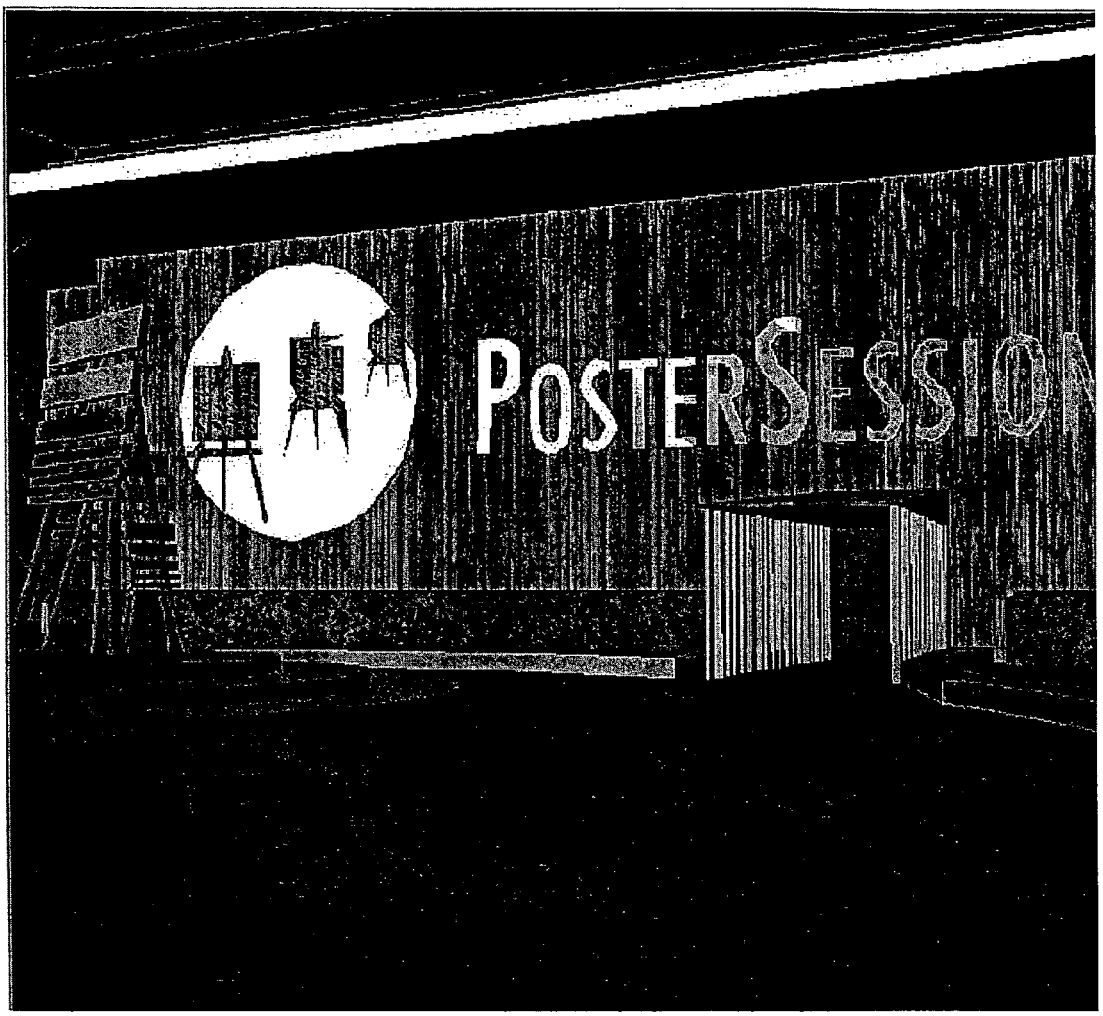
FIG. 22 shows the entrance of the Poster Room of Medtradeshow.
Figure 23:
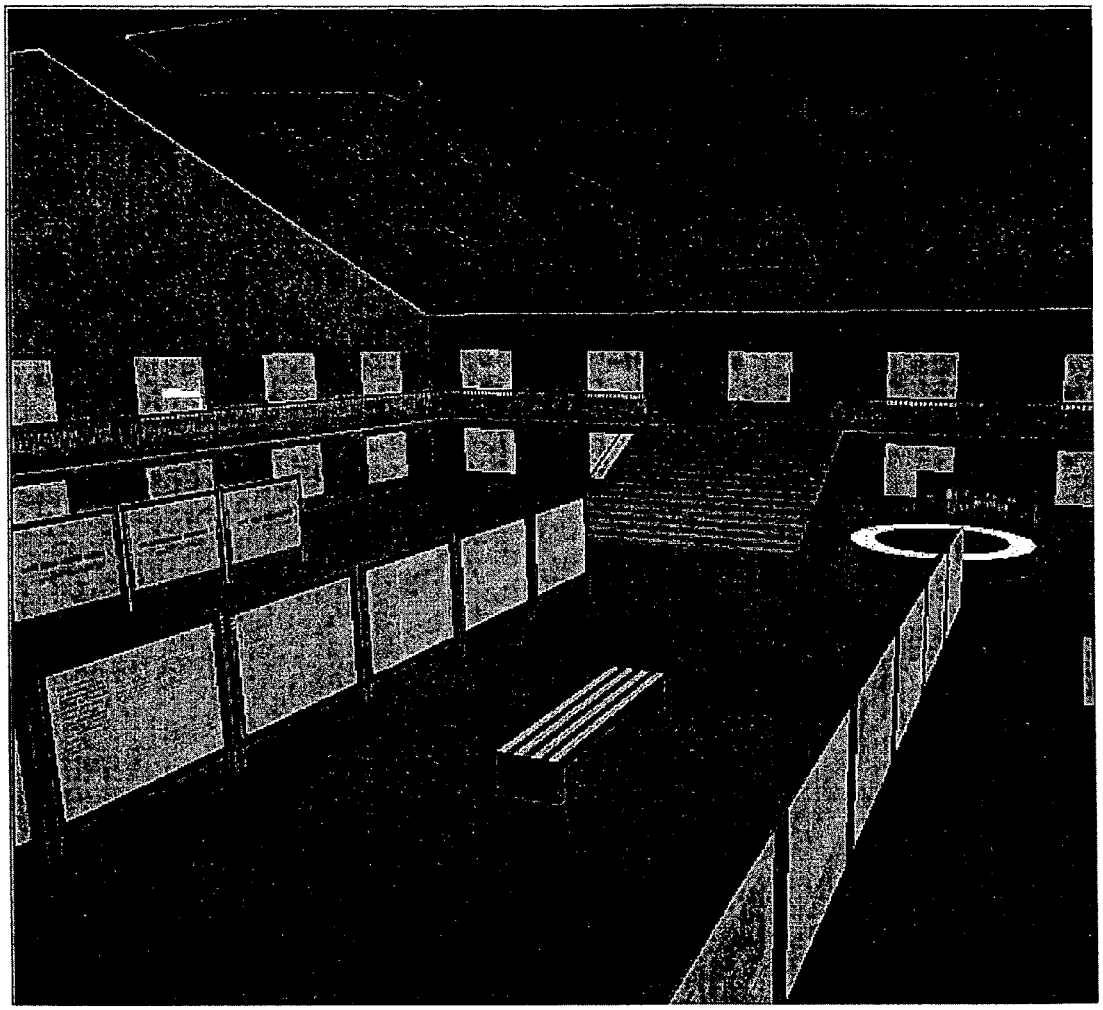
FIG. 23 shows the inside of the Poster Room of Medtradeshow.
Figure 24:
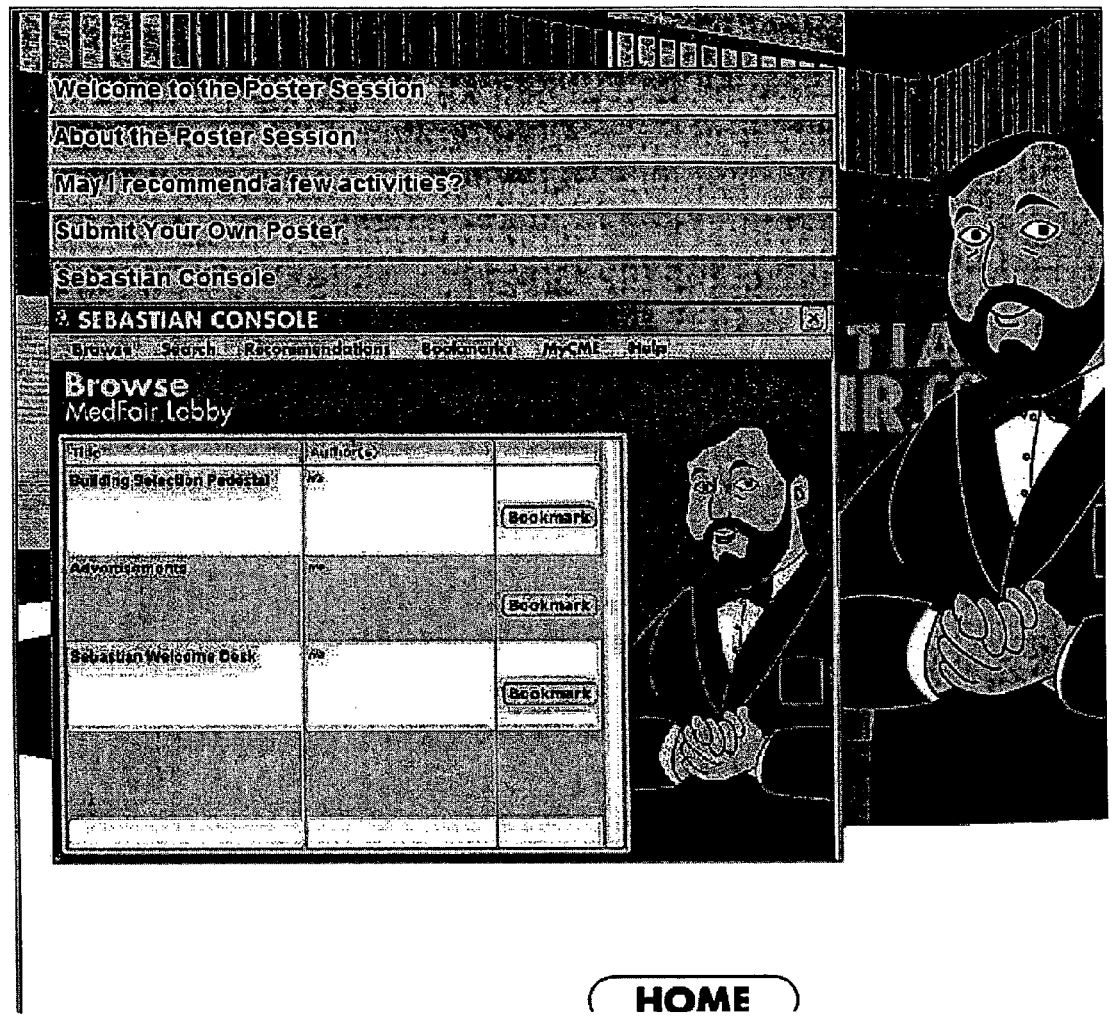
FIG. 24 shown a Concierge menu screen available in the Poster Room.

It is filled with virtual posters with visual, self-explanatory presentations of recent research findings interesting to participants of the healthcare industry. An Attendee may enter a poster room designated for a particular subject matter, such as rating scales/assessment tools for delivering mental health care services. FIG. 22 shows the entrance of the Poster Room of Medtradeshow. In such a poster room (FIG. 23), posters regarding practice-based research, scholarly subject reviews, and straightforward case reviews (including case studies, controlled studies, clinical observations, critical overviews, pilot studies, open trials, chart reviews, and case series with literature reviews) are displayed. The Attendee can directly click to view a poster, then retrieve the full article by another click which will bring up a .pdf file of the article. Alternatively, the Attendee can click for a Concierge menu screen available in the Poster Room (FIG. 24) for introduction and recommendations for the Poster Room. In other words, a poster room may be organized and assembled for the Attendee on demand.

The Attendee may click a Search bottom on a menu bar on the top of the display screen (or a menu icon which will expend after being clicked) to change the number of posters displayed in the poster room by keywords or phrases, such as Attention Deficit Hyperactivity Disorder (ADHD). The Attendee may also reduce or increase the number of posters displayed in the poster room by additional requests. Rather than visiting an exiting poster room, the Attendee may organize a new poster room under a new subject matter by retrieving posters by keywords or phrases, such as Kiddie-SADS for young children with evidence of ADHD.

The basic elements of each poster include the following sections: Title, Authorship, Acknowledgments, Abstract (Background, Method, Results, and Conclusion), Introduction and Method, Results, Conclusion, References. The Abstract (in one webpage) is displayed as default at the first click of the Attendee after entering the poster room.

Any participants of the healthcare industry may submit a poster that meet the scope and submission criteria, such as Uniform Requirements for Manuscripts Submitted to Biomedical Journals developed by the International Committee of Medical Journal Editors (available at: www.icmje.org). The submitted poster will be sent to an expert consultant for peer review. Once the poster is accepted, Medtradeshow will notify the author via at least one of the communication vehicles about an approximate publication date on Medtradeshow. If the poster is rejected, Medtradeshow will also notify the author via at least one of the communication vehicles with a brief explanation for the rejection. Posters may receive a light copyedit intended to correct spelling and grammatical errors. The author is responsible for ensuring that the data are accurate and the presentation is consistent.

Medtradeshow offers the author opportunities to update the information in a published poster by linking certain keywords in the poster to a on-line information source such as the regulating authority FDA or a library so as to synchronize the content.

Office Management Room

It provides a forum for Attendees to obtain office practice information, systems, policies, procedures, software, reimbursement information, medical record information, bill information, and opinions on how to manage means and solve problems in terms of their office practices or other managerial activities except disease management which will be treated separately in the Disease Management room.

Disease Management Room

Disease Management is a program that will include a treatment process for various disease states that generally includes physician or healthcare professional participation. It generally is a broad approach to appropriate coordination of the entire disease treatment process that often involves shifting away from more expensive inpatient and acute care to areas such as medication compliance, diet compliance, preventive medicine, patient counseling and education, and outpatient care. The Disease Management room provides a process for Attendees to better manage the treatment of patients. As with the Continuing Education room, the information provided in the Disease Management room is not controlled by or influenced by any manufacturers of medical equipment, devices, or pharmaceutical products.

Tele-Medicine Room

Tele-medicine provides access to healthcare professionals via telecommunications technology to more expert healthcare professionals who can assist in the treatment of a patient. Such a characteristic distinguishes the Tele-Medicine Room from the Case Conference Room and the Continuing Education room. Similar to the Continuing Education room, the information provided in the Tele-Medicine room.

Post Medtradeshow Feature

With existing data mining algorithms of the invention, Medtradeshow develops in-depth information based upon preliminary information provided by the participant during the registration, additional personal information available from other sources, and the Attendee's visiting history of Medtradeshow. Medtradeshow responds to the Attendee's questions directly and quickly (even real-time). All data collected by Medtradeshow will be assembled, stored, correlated or otherwise processed for Medtradeshow in accordance with all Federal and State Privacy and Confidentiality Laws and Regulations.

Medtradeshow develops informatics from the personal information and visiting history of the Attendee by gathering, manipulating, storing, retrieving and classifying recorded information. It includes the use of computers and software to improve communication, understanding and management of information interesting to the participants of the healthcare industry. To facilitate the informational and transaction activities in Medtradeshow, Medtradeshow applies existing data mining algorithms for customized programs or services. Data mining, or knowledge discovery uncovers hidden patterns and relationships among data. Meaningful information or transactional attributes, such as consumption profiles, habits and preferences of Attendees, is extracted from internal and external databases through advanced statistical analysis and modeling techniques. Data mining is available for exhibitors, continuation education providers, speakers, etc. that want to improve the quality of programs and services and gain advantage and improvement by exploiting the data available via Medtradeshow. Using Attendee visiting history analysis to improve continuation education activities to meet the Attendee's need.

Participants may choose to receive follow up information, answer surveys and questionnaires and track their transactions or interests via communication vehicles in conjunction with the optional features of concierge, e-LERTS, detailing, celebrity Pop-Ups, Case conferencing, Tele-Medicine, Continuing Education, Use of Advisory Panels, Needs Assessment, Office Management and Disease Management. For example, through e-LERTS, the invention provides each authorized Attendee, after their departure from the site, the opportunity to purchase authorized products and services and order copies of enduring materials. In addition, the combination of input from the experts, advisory panels along with suggestions from Attendees as to what subjects they feel need addressing will provide an important objective element to update the operation of the Medtradeshow.

What is claimed is:

1. A system for providing a virtual healthcare industry trade show via internet, comprising:
   at least one server computer for providing healthcare sources of information, products or services desired by participants of the healthcare industry trade show, said at least one server computer having an access-limiting software element for conditionally controlling access to said healthcare industry trade show by said participants, said access-limiting software element of said at least one server computer including a verification and authorization software component including computer-executable instructions for limiting access to said virtual healthcare trade show based on access-limiting requirements from individual healthcare sources, on access-limiting requirements of applicable laws and regulations, and on access-determining credential data provided by each of said participants and attendees so as to ensure that each of said participants of the healthcare industry and said attendees is appropriately authorized to conduct transactions of access-limited information, products or services with other so authorized participants of the healthcare industry trade show or attendees;
   at least one other computer used by any of said participants of the healthcare industry connected via internet or intranet to said at least one server computer to conduct transactions via said healthcare industry trade show; and
   a plurality of communication vehicles adapted to be selectably used by attendees of said healthcare industry trade show, and operatively connectable to communicate directly with and through said at least one server computer via the internet so as to conduct transactions with at least one of said healthcare sources and said participants via said healthcare industry trade show, wherein communication between any of said healthcare sources and participants of the healthcare industry facilitated through said at least one server computer with said attendees and others of said participants of the healthcare industry uses any of said plurality of communication vehicles, at the option of any of said participants of the healthcare industry or said attendees, whereby said communication between said healthcare sources, said participants and said attendees form a virtual trade show independent of any non-virtual activities in the healthcare industry, and
   said server computer includes:
   a software component and data storage configured to create virtual representations of facilities of said healthcare industry trade show and for supporting different browsers of said at least one other computer to view said virtual representations;
   a software component and data storage configured to facilitate an attendee signing off any facility or any activity in progress and then returning to said facility or activity to resume the visit or activity at the same location, timing to continue visit the facility or resuming the activity without starting from the beginning of the visit or activity; and
   a software component and data storage configured to collect and disseminate FDA permitted off-label product promotions which are scientific and educational in nature to medical community as delivered by independent third parties in the formats of clinical trials, special studies, and grand rounds.

2. The system for providing a virtual healthcare industry trade show via internet according to claim 1, wherein said server computer further includes a software component and data storage configured to play per-recorded corresponding information when a selected one of displayed facilities is being shown.

3. The system for providing a virtual healthcare industry trade show via internet according to claim 1, wherein said server computer further includes a software component and data storage configured to provide and display a menu icon for bringing out a menu bar or calling up a Concierge menu screen, said menu bar or menu screen having bottom for browse, search, bookmark, or ask for recommendation, or to view facilities visited by an Attendee previously.

4. The system for providing a virtual healthcare industry trade show via internet according to claim 1, wherein said server computer further includes a software component and data storage configured to update displayed information in said healthcare industry trade show by revising from said at least one other computer.

5. The system for providing a virtual healthcare industry trade show via internet according to claim 1, wherein said server computer further includes a software component and data storage configured to link at least one keyword, or paragraph, or article in displayed information to a on-line information source to thereby synchronize contents thereof.

6. The system for providing a virtual healthcare industry trade show via internet according to claim 1, wherein said server computer further includes a software component and data storage configured to collect and display most frequented browsed articles, class, lecture, booth, room, or hall by predetermined categories or sub-categories of said participants of the healthcare industry.

7. The system for providing a virtual healthcare industry trade show via internet according to claim 1, wherein said server computer further includes a software component and data storage configured to collect and display recommended articles, class, lecture, booth, room, or hall by predetermined categories or sub-categories of exhibitors which sponsor virtual booths in said healthcare industry trade show.

8. The system for providing a virtual healthcare industry trade show via internet according to claim 1, wherein said server computer further includes a software component and data storage configured to collect and display a number of virtual posters with visual, self-explanatory presentations of recent research findings interesting to participants of the healthcare industry in a virtual poster room.

9. The system for providing a virtual healthcare industry trade show via internet according to claim 8, wherein said poster room is predetermined to designate for a particular subject matter by said healthcare industry trade show or is organized and assembled for an attendee on demand.

10. The system for providing a virtual healthcare industry trade show via internet according to claim 8, wherein said server computer further includes a software component and data storage configured to reduce or increase the number of virtual posters in the poster room based upon a request by an attendee.

11. The system for providing a virtual healthcare industry trade show via internet according to claim 8, wherein said server computer further includes a software component and data storage configured to change the virtual posters in the poster room based upon a search requested by an attendee.

12. The system for providing a virtual healthcare industry trade show via internet according to claim 1, wherein said server computer further includes a software component and data storage for data mining configured to develop in-depth attendee information based upon preliminary information provided by the attendee during registration, additional personal information available from other sources, and Attendee's visiting history of said healthcare industry trade show.

13. The system for providing a virtual healthcare industry trade show via internet according to claim 1, wherein the software component and data storage are configured to create 3-D visual virtual representations of the facilities of said healthcare industry trade show and for supporting different browsers of said at least one other computer to view said 3-D visual virtual representations.

14. A system for providing a virtual healthcare industry trade show via internet, comprising:
at least one server computer for providing healthcare sources of information, products or services desired by participants of the healthcare industry trade show, said at least one server computer having an access-limiting software element for conditionally controlling access to said healthcare industry trade show by said participants, said access-limiting software element of said at least one server computer including a verification and authorization software component including computer-executable instructions for limiting access to said virtual healthcare trade show based on access-limiting requirements from individual healthcare sources, on access-limiting requirements of applicable laws and regulations, and on access-determining credential data provided by each of said participants and attendees so as to ensure that each of said participants of the healthcare industry and said attendees is appropriately authorized to conduct transactions of access-limited information, products or services with other so authorized participants of the healthcare industry trade show or attendees;
at least one other computer used by any of said participants of the healthcare industry connected via internet or intranet to said at least one server computer to conduct transactions via said healthcare industry trade show; and
a plurality of communication vehicles adapted to be selectably used by attendees of said healthcare industry trade show, and operatively connectable to communicate directly with and through said at least one server computer via the internet so as to conduct transactions with at least one of said healthcare sources and said participants via said healthcare industry trade show, wherein communication between any of said healthcare sources and participants of the healthcare industry facilitated through said at least one server computer with said attendees and others of said participants of the healthcare industry uses any of said plurality of communication vehicles, at the option of any of said participants of the healthcare industry or said attendees, whereby said communication between said healthcare sources, said participants and said attendees form a virtual trade show independent of any non-virtual activities in the healthcare industry, and
said server computer includes
a software component and data storage configured to create a virtual Continuing Education facility for providing continuing education to said participants of the healthcare industry;
a software component and data storage configured to facilitate an attendee signing off any facility or any activity in progress and then returning to said facility or activity to resume the visit or activity at the same location, timing to continue visit the facility or resuming the activity without starting from the beginning of the visit or activity; and
a software component and data storage configured to collect and disseminate FDA permitted off-label product promotions which are scientific and educational in nature to medical community as delivered by independent third parties in the formats of clinical trials, special studies, and grand rounds.

15. The system for providing a virtual healthcare industry trade show via internet according to claim 14, wherein said server computer further includes a software component and data storage configured to determine behavioral outcomes as a result of attending a Continuing Educational activity by comparing surveyed attendee behavior before and after attending the activity.

16. The system for providing a virtual healthcare industry trade show via internet according to claim 14, wherein said server computer further includes a software component and data storage configured to play per-recorded corresponding speech when a selected virtual classroom or lecture hall is being shown.

17. The system for providing a virtual healthcare industry trade show via internet according to claim 14, wherein said server computer further includes a software component and data storage configured to generate and display a sub-screen for showing a presentation outline of said speech of an ongoing class or lecture.

18. The system for providing a virtual healthcare industry trade show via internet according to claim 14, wherein said server computer further includes a software component and data storage configured to manipulate said outline to be scrolled up or down for different slides or screenshots in conjunction with recorded speech corresponding with each slide or screenshot.

19. The system for providing a virtual healthcare industry trade show via internet according to claim 14, wherein said server computer further includes a software component and data storage configured to provide and display a menu icon for bringing out a menu bar or calling up a Concierge menu screen, said menu bar or menu screen having bottoms for browse, search, bookmark a class or lecture, or ask for recommendation, or to view classes or lectures taken by an Attendee previously.

20. The system for providing a virtual healthcare industry trade show via internet according to claim 14, wherein the software component and the data storage are configured to create a 3-D virtual Continuing Education facility for providing continuing education to said participants of the healthcare industry.

21. A system for providing a virtual healthcare industry trade show via interne, comprising:

at least one server computer for providing healthcare sources of information, products or services desired by participants of the healthcare industry trade show, said at least one server computer having an access-limiting software element for conditionally controlling access to said healthcare industry trade show by said participants, said access-limiting software element of said at least one server computer including a verification and authorization software component including computer-executable instructions for limiting access to said virtual healthcare trade show based on access-limiting requirements from individual healthcare sources, on access-limiting requirements of applicable laws and regulations, and on access-determining credential data provided by each of said participants and attendees so'as to ensure that each of said participants of the healthcare industry and said attendees is appropriately authorized to conduct transactions of access-limited information, products or services with other so authorized participants of the healthcare industry trade show or attendees;

at least one other computer used by any of said participants of the healthcare industry connected via internet or intranet to said at least one server computer to conduct transactions via said healthcare industry trade show; and a plurality of communication vehicles adapted to be selectably used by attendees of said healthcare industry trade show, and operatively connectable to communicate directly with and through said at least one server computer via the internet so as to conduct transactions with at least one of said healthcare sources and said participants via said healthcare industry trade show, wherein communication between any of said healthcare sources and participants of the healthcare industry facilitated through said at least one server computer with said attendees and others of said participants of the healthcare industry uses any of said plurality of communication vehicles, at the option of any of said participants of the healthcare industry or said attendees, whereby said communication between said healthcare sources, said participants and said attendees form a virtual trade show independent of any non-virtual activities in the healthcare industry, wherein said server computer includes a software component and data storage configured to create virtual representations of facilities of said healthcare industry trade show and for supporting different browsers of said at least one other computer to view said virtual representations;

a software component and data storage configured to facilitate an attendee signing off any facility or any activity in progress and then returning to said facility or activity to resume the visit or activity at the same location, timing to continue visit the facility or resuming the activity without starting from the beginning of the visit or activity; and a software component and data storage configured to collect and disseminate FDA permitted off-label product promotions which are scientific and educational in nature to medical community as delivered by independent third parties in the formats of clinical trials, special studies, and grand rounds.

22. The system for providing a virtual healthcare industry trade show via internet according to claim 21, wherein said software component and data storage are further configured to disseminate as initiated by a manufacturer of the off-label product or requested by an attendee of said healthcare industry trade show.

23. The system for providing a virtual healthcare industry trade show via internet according to claim 21, wherein the software component and the data storage are configured to create 3-D visual virtual representations of facilities of said healthcare industry trade show and for supporting different browsers of said at least one other computer to view said 3-D visual virtual representations.

* * * * *